United States Patent
Duke et al.

(10) Patent No.: US 10,722,650 B2
(45) Date of Patent: Jul. 28, 2020

(54) SYSTEM AND METHOD FOR ADJUSTING THERAPY BASED ON RISK ASSOCIATED WITH A GLUCOSE STATE

(71) Applicant: Roche Diagnostics Operations, Inc., Indianapolis, IN (US)

(72) Inventors: David L. Duke, Fishers, IN (US); Abhishek S. Soni, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 951 days.

(21) Appl. No.: 14/229,016

(22) Filed: Mar. 28, 2014

(65) Prior Publication Data
US 2015/0273147 A1    Oct. 1, 2015

(51) Int. Cl.
*A61M 5/172* (2006.01)
*A61M 5/142* (2006.01)
*G06F 19/00* (2018.01)
*G16H 50/30* (2018.01)
(Continued)

(52) U.S. Cl.
CPC ....... *A61M 5/1723* (2013.01); *A61B 5/14532* (2013.01); *A61B 5/4836* (2013.01); *A61M 5/14244* (2013.01); *G06F 19/3456* (2013.01); *G06F 19/3468* (2013.01);
(Continued)

(58) Field of Classification Search
CPC ............ A61M 5/1723; A61M 5/14244; A61M 2005/14208; A61M 2205/52; A61M 2230/201; A61B 5/14532; A61B 5/4836
See application file for complete search history.

(56) References Cited

U.S. PATENT DOCUMENTS

| 6,572,545 B2 | 6/2003 | Knobbe et al. |
| 6,923,763 B1 | 8/2005 | Kovatchev et al. |
| 9,247,901 B2 | 2/2016 | Kamath et al. |
| (Continued) | | |

FOREIGN PATENT DOCUMENTS

| WO | WO2010/099313 | 9/2010 |
| WO | 2013/090709 A1 | 6/2013 |

OTHER PUBLICATIONS

International Preliminary Report on Patentability received from the International Bureau of WIPO, dated Oct. 4, 2016, for International Application No. PCT/US2015/023007; 10 pages.
(Continued)

*Primary Examiner* — Nathan R Price
*Assistant Examiner* — Justin L Zamory
(74) *Attorney, Agent, or Firm* — Faegre Drinker Biddle & Reath LLP

(57) ABSTRACT

The present disclosure relates to a system and method for determining a basal rate adjustment based on risk associated with a glucose state of a person with diabetes. A method may include detecting a glucose state of the person based on a received glucose measurement signal and determining a current risk metric associated with the detected glucose state. The method may include identifying a reference glucose state and a reference risk metric associated with the reference glucose state, and calculating an adjustment to a basal rate of a therapy delivery device based on the current risk metric associated with the detected glucose state and the reference risk metric associated with the reference glucose level.

23 Claims, 15 Drawing Sheets

(51) Int. Cl.
  *A61B 5/145* (2006.01)
  *A61B 5/00* (2006.01)
(52) U.S. Cl.
  CPC ... *G16H 50/30* (2018.01); *A61M 2005/14208* (2013.01); *A61M 2205/52* (2013.01); *A61M 2230/201* (2013.01)

(56) References Cited

U.S. PATENT DOCUMENTS

| | | | |
|---|---|---|---|
| 2010/0056992 | A1 | 3/2010 | Hayter |
| 2010/0174228 | A1 | 7/2010 | Buckingham et al. |
| 2011/0184267 | A1 | 8/2011 | Duke et al. |
| 2011/0313390 | A1 | 12/2011 | Roy et al. |
| 2011/0313674 | A1 | 12/2011 | Duke et al. |
| 2013/0041342 | A1 | 2/2013 | Bernini et al. |
| 2014/0039383 | A1* | 2/2014 | Dobbles ............ A61M 15/0065 604/66 |
| 2014/0058237 | A1 | 2/2014 | Galley et al. |

OTHER PUBLICATIONS

Patek, S.D., et al., "Modular Closed-Loop Control of Diabetes," IEEE Trans Biomed Eng., Nov. 2012, vol. 59, No. 11: 2986-2999, available on the Internet as of Dec. 18, 2017 at https://www.ncbi.nlm.nih.gov/PMC/articles/PMC4607512/pdf/nihms725377.pdf.

Cameron, Fraser, et al. "A Closed Loop Artificial Pancreas Based on Risk Management", Journal of Diabetes Science and Technology: vol. 5, issue 2, Mar. 2011, pp. 368-379.

Kovatchev, Boris, et al. "Symmetrization of the Blood Glucose Measurement Scale and Its Applications", Diabetes Care: vol. 20, No. 11, Nov. 1997, pp. 1655-1658.

Guerra, Stefania, et al. "A Dynamic Risk Measure from Continuous Glucose Monitoring Data", Diabetes Technology & Therapeutics, vol. 13, No. 8, 2011, pp. 843-853.

Wang, et al.; "Automatic Bolus and Adaptive Basal Algorithm for the Artificial Pancreatic β-Cell", Wang, et al., Diabetes Technology & Therapeutics, vol. 12, No. 11, 2010.

Wang, et al.; "A Novel Adaptive Basal Therapy Based on the Value and Rate of Change of Blood Glucose"; Journal of Diabetes Science & Technology, vol. 3, Issue 5, Sep. 2009.

Eren-Oruklu, M et al. Hypoglycemia Prediction with Subject-Specific Recursive Time-Series Models. Journal of Diabetes Science and Technology, vol. 4, No. 1, Jan. 2010, pp. 25-33.

International Search Report and Written Opinion received for PCT Patent Application No. PCT/US2015/023007, dated Jun. 29, 2015, 11 pages.

Thomson, MC et al. Mapping Malaria Risk in Africa: What can Satellite Data Contribute? Parasitology Today, vol. 13, No. 8, 1997, pp. 313-318.

* cited by examiner

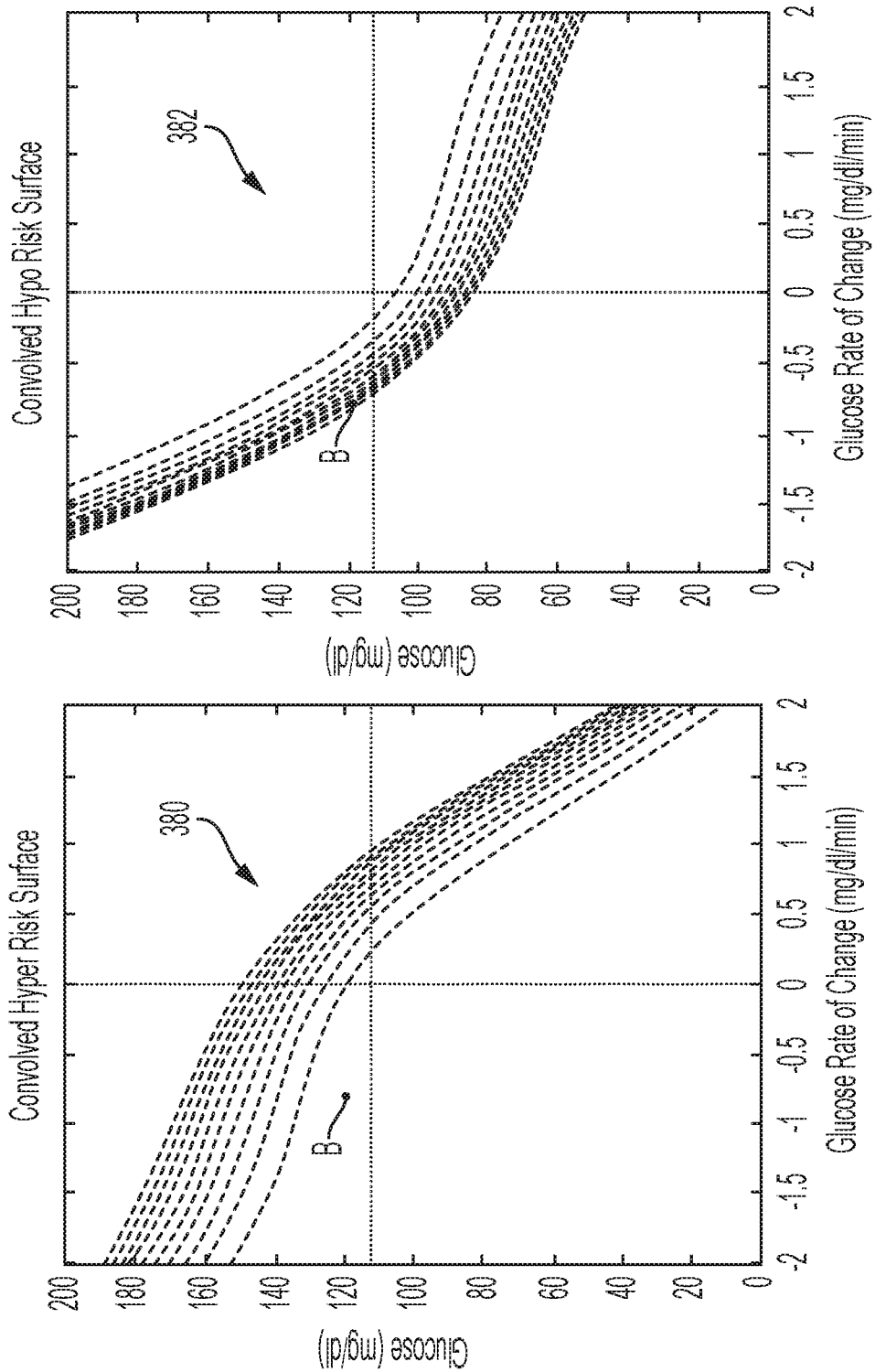

SYSTEM AND METHOD FOR ADJUSTING THERAPY BASED ON RISK ASSOCIATED WITH A GLUCOSE STATE

TECHNICAL FIELD

The present disclosure relates generally to diabetes care medical systems and methods used for diagnostics and therapy, and in particular to systems and methods for assessing risk associated with a glucose state and adjusting therapy based on the risk.

BACKGROUND

Many people suffer from Type I or Type II diabetes, in which the body does not properly regulate the blood glucose level. A continuous glucose monitor (CGM) allows the blood glucose level of a patient with diabetes to be measured on an ongoing basis, such as every few minutes. The timing and dosage of insulin to administer to the patient may be determined on the basis of measurements recorded by the CGM device. Glucose readings from CGM devices are displayed to the patient, and the patient can inject insulin or consume meals to help control the glucose level. Insulin pumps can deliver precise insulin dosages on a programmable schedule which may be adjusted by the patient or health care provider.

Hazard metrics may be derived from glucose data for assessing a hazard to the diabetic person based on a detected glucose level. For example, a known hazard metric includes the hazard function proposed in the following paper: Kovatchev, B. P. et al., *Symmetrization of the blood glucose measurement scale and its applications*, Diabetes Care, 1997, 20, 1655-1658. The Kovatchev hazard function is defined by the equation $h(g)=[1.509(\log(g))^{1.0804}-5.381)]^2$, wherein g is the blood glucose concentration (in milligrams per deciliter or mg/dl) and h(g) is the corresponding penalty value. The Kovatchev function provides a static penalty (i.e., hazard) value in that the penalty depends only on the glucose level. The minimum (zero) hazard occurs at 112.5 mg/dl. The hazard with the glucose level approaching hypoglycemia rises significantly faster than the hazard with the glucose level approaching hyperglycemia.

The Kovatchev hazard function fails to account for the rate of change of the glucose level as well as the uncertainty associated with the measured glucose level. For example, a patient's hazard associated with 100 mg/dl and a rapidly falling blood glucose level is likely greater than the patient's hazard associated with 100 mg/dl with a constant glucose rate of change. Further, measured glucose results may be inaccurate due to sensor noise, sensor malfunction, or detachment of the sensor.

Various approaches have been made to control the glucose levels of diabetic people based on CGM glucose data. One approach for limiting the occurrence of hypoglycemic conditions includes an insulin pump shutoff algorithm that completely shuts off the basal insulin if the CGM glucose level drops below a low glucose threshold, such as 50 to 70 mg/dl, and later resumes the basal insulin after a few hours. However, this on/off approach adversely requires the adverse condition of crossing the low glucose threshold to occur before action is taken. Further, this approach does not take into account the speed with which the glucose is crossing the threshold, which may be problematic for patients (e.g., children, active individuals, etc.) with a high rate of glucose change.

Another approach is to alert the patient of predicted hypoglycemia, and the patient then consumes an amount of carbohydrates and waits a predetermined time period. If the system still predicts hypoglycemia the patient repeats the cycle until the system no longer predicts hypoglycemia. However, this approach makes the assumption that the patient is able to consume carbohydrates immediately upon being alerted of the predicted hypoglycemia. Further, the patient may overcorrect by consuming too many carbs, possibly leading to weight gain or to trending the glucose levels towards hyperglycemia.

Accordingly, some embodiments of the present disclosure provide a predictive approach for adjusting a therapy basal rate by mapping the risk of the estimated glucose state to an adjustment of the basal rate based on an aggressiveness factor. Risk associated with the glucose state is based on the blood glucose level, the rate of change of the blood glucose level, and the uncertainty associated with the blood glucose level and rate of change. Further, some embodiments provide for adjusting the calculated risk for a glucose state in response to a meal bolus, an insulin bolus, and/or other events that may affect the risk of hypoglycemia or hyperglycemia.

SUMMARY

In an exemplary embodiment of the present disclosure, a method of determining a basal rate adjustment based on risk associated with a glucose state of a person with diabetes is provided. The method includes receiving, by at least one computing device, a signal representative of at least one glucose measurement. The method includes detecting, by the at least one computing device, a glucose state of the person based on the signal. The detected glucose state includes a glucose level of the person and a rate of change of the glucose level. The method further includes determining, by the at least one computing device, a current risk metric associated with the detected glucose state based on a target glucose state. The target glucose state is stored in memory accessible by the at least one computing device. The current risk metric indicates a risk of at least one of a hypoglycemic condition and a hyperglycemic condition of the person. The method further includes identifying, by the at least one computing device, a reference glucose state and a reference risk metric associated with the reference glucose state. The method further includes calculating, by the at least one computing device, an adjustment to a basal rate of a therapy delivery device based on the current risk metric associated with the detected glucose state and the reference risk metric associated with the reference glucose level.

In another exemplary embodiment of the present disclosure, a blood glucose management device is provided. The blood glucose management device is configured to determine a basal rate adjustment based on risk associated with a glucose state of a person with diabetes. The device includes a non-transitory computer-readable medium storing executable instructions. The device further includes at least one processing device configured to execute the executable instructions such that, when executed by the at least one processing device, the executable instructions cause the at least one processing device to receive a signal representative of at least one glucose measurement. The executable instructions further cause the at least one processing device to detect a glucose state of the person based on the signal. The detected glucose state includes a glucose level of the person and a rate of change of the glucose level. The executable instructions further cause the at least one processing device to determine a current risk metric associated with the detected glucose state. The current risk metric indicates a risk of at least one of a hypoglycemic condition and a hyperglycemic condition of the person. The executable instructions further cause the at least one processing device to identify a reference glucose state and a reference risk metric associated with the reference glucose state. The executable instructions further cause the at least one processing device to calculate an adjustment to a basal rate of a therapy delivery device based on the current risk metric associated with the detected glucose state and the reference risk metric associated with the reference glucose level.

BRIEF DESCRIPTION OF THE DRAWINGS

The features and advantages of the present invention will become more apparent to those skilled in the art upon consideration of the following detailed description taken in conjunction with the accompanying figures, wherein

FIG. 16 illustrates a hyperglycemic risk surface that is convolved from the risk surface of FIG. 6 assuming constant uncertainty;

FIG. 17 illustrates a hypoglycemic risk surface that is convolved from the risk surface of FIG. 7 assuming constant uncertainty;

DETAILED DESCRIPTION

Figure 1:
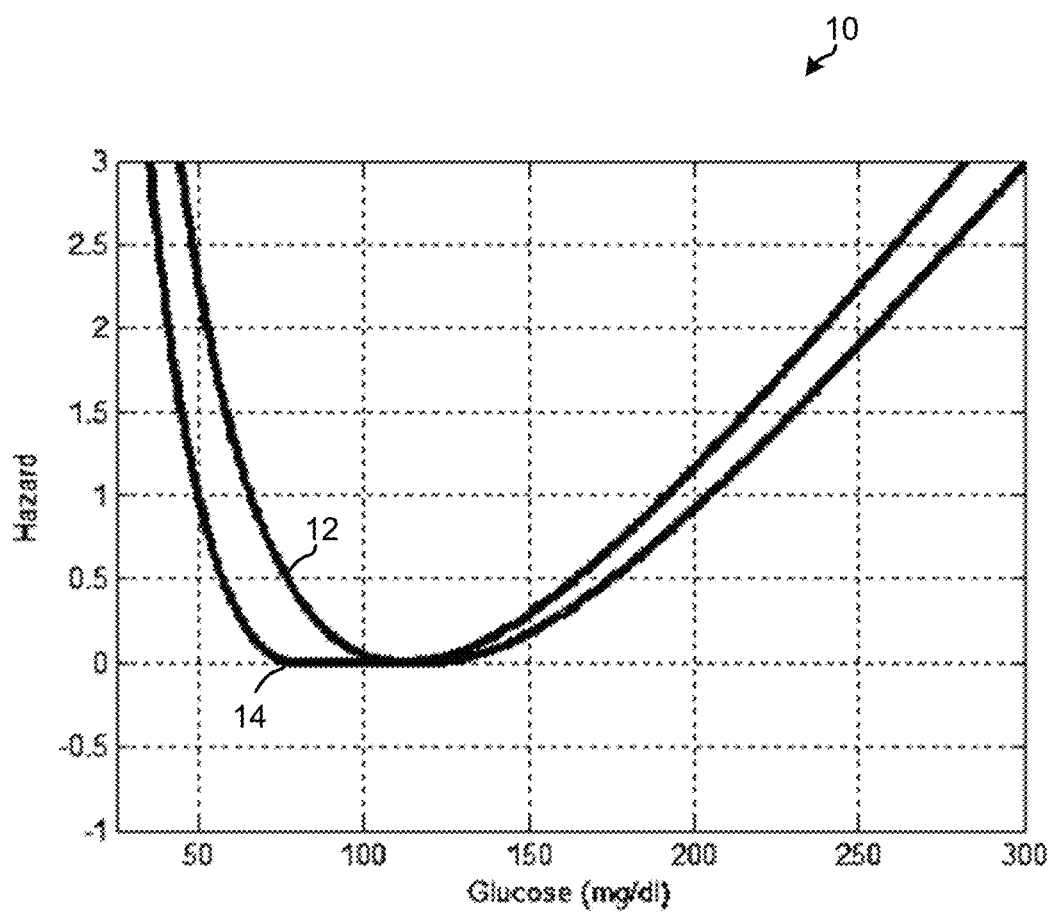
FIG. 1 illustrates an exemplary hazard function for assessing the hazard associated with a glucose level.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

As used herein, the "measured glucose values" or "measured glucose results" are the glucose levels of the person as measured by a glucose sensor; the "actual glucose level" is the actual glucose level of the person; and the "estimated glucose level" is the estimated glucose level of the person, which may be based on the measured glucose values and the probability of sensor accuracy.

The term "logic" or "control logic" or "module" as used herein may include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion and would remain in accordance with the embodiments herein disclosed.

FIG. 1 illustrates an exemplary hazard function 10 for calculating a static penalty value for a given glucose level. The hazard function 10 is defined by the following equation:

$$h(g) = \begin{cases} 0, & g_1 \le g \le g_2 \\ \alpha(\log(g)^c - \log(g_2)^c), & g_2 < g \\ \alpha\left(\log(g)^{\frac{\log(\beta)}{\log(\log(g_1))}} - \beta\right), & g_1 > g \end{cases} \quad (1)$$

wherein g is the blood glucose level (mg/dl) shown on the x-axis, h(g) is the corresponding static penalty value shown on the y-axis, and $g_1$ and $g_2$ are glucose levels used to define a range of target glucose values ($g_1 \le g \le g_2$) or a single target glucose value ($g_1 = g_2$). In the illustrated embodiment, the variables α, β, and c are defined as follows: α=1.509, β=5.381, and c=1.084. The range of target glucose values ($g_1 \le g \le g_2$) illustratively has a corresponding penalty value of zero, as shown with equation (1). With the target glucose level $g_1 = g_2 = 112.5$ mg/dl, hazard function 10 generates a hazard curve 12 corresponding to the Kovatchev function. With an exemplary target glucose range defined by $g_1 = 75$ mg/dl and $g_2 = 125$ mg/dl, hazard function 10 generates a hazard curve 14. Hazard curve 14 illustratively provides penalty values for a given glucose state when the target glucose range is defined from 75 mg/dl to 125 mg/dl. Other suitable target glucose levels/ranges and penalty values corresponding to the target glucose levels/ranges may be provided with equation (1).

Figure 2:
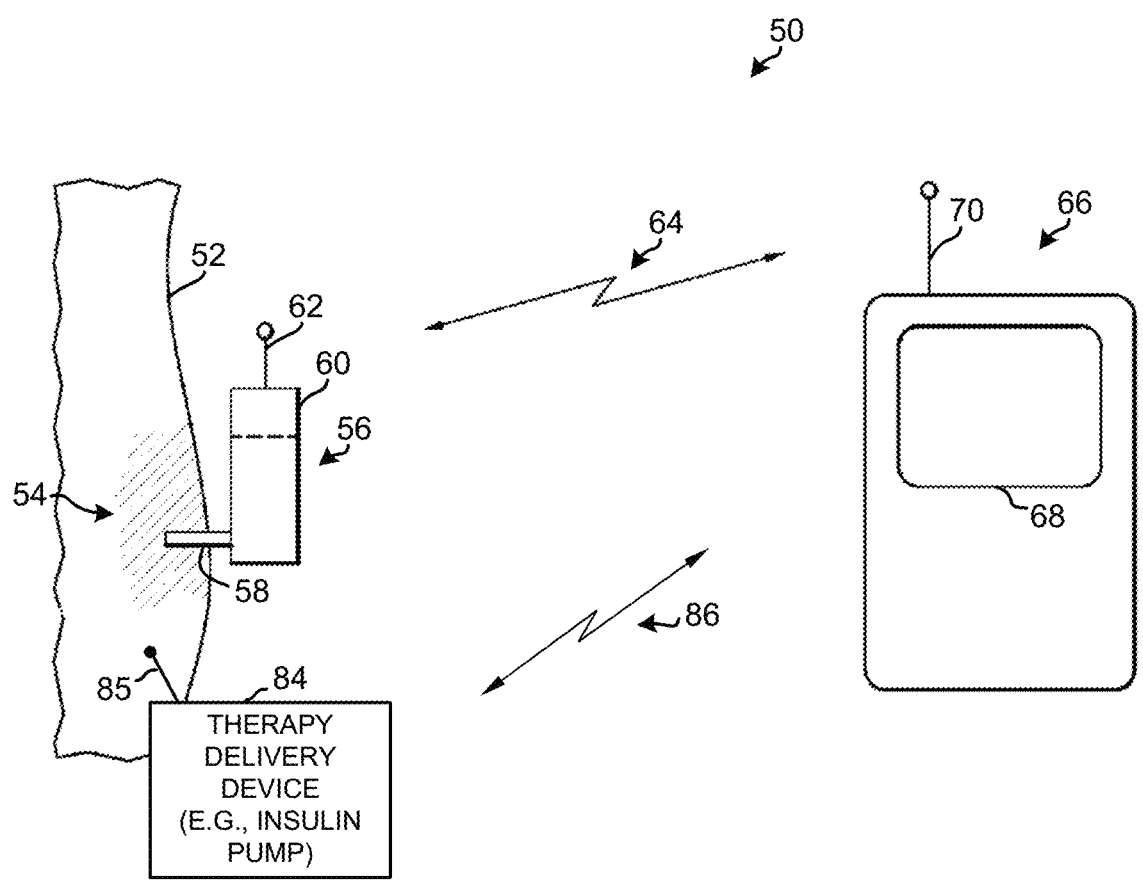
FIG. 2 illustrates a continuous glucose monitoring (CGM) system according to one or more embodiments described herein.

Referring to FIG. 2, an exemplary continuous glucose monitoring (CGM) system 50 is illustrated for monitoring the glucose level of a person having diabetes. In particular, CGM system 50 is operative to collect a measured glucose value at a predetermined, adjustable interval, such as every one minute, five minutes, or at other suitable intervals. CGM system 50 illustratively includes a glucose sensor 56 having a needle or probe 58 that is inserted under the skin 52 of the person. The end of the needle 58 is positioned in interstitial fluid 54, such as blood or another bodily fluid, such that measurements taken by glucose sensor 56 are based on the level of glucose in interstitial fluid 54. Glucose sensor 56 is positioned adjacent the abdomen of the person or at another suitable location. Glucose sensor 56 may comprise other components as well, including but not limited to a wireless transmitter 60 and an antenna 62. Glucose sensor 56 may alternatively use other suitable devices for taking measurements, such as, for example, a non-invasive device (e.g., infrared light sensor). Upon taking a measurement, glucose sensor 56 transmits the measured glucose value via a communication link 64 to a computing device 66, illustratively a blood glucose management device 66.

CGM system 50 further includes a therapy delivery device 84, illustratively an insulin infusion pump 84, for delivering therapy (e.g., insulin) to the person. Insulin pump 84 is in communication with management device 66 via a communication link 86, and management device 66 is able to communicate bolus and basal rate information to insulin pump 84. Insulin pump 84 includes a catheter 85 having a needle that is inserted through the skin 52 of the person for injecting the insulin. Insulin pump 84 is illustratively positioned adjacent the abdomen of the person or at another suitable location. Similar to glucose sensor 56, infusion pump 84 also includes a wireless transmitter and an antenna for communication with management device 66. Insulin pump 84 is operative to deliver basal insulin (e.g., small doses of insulin continuously or repeatedly released at a basal rate) and bolus insulin (e.g., a surge dose of insulin, such as around a meal event, for example). The bolus insulin may be delivered in response to a user input triggered by the user, or in response to a command from management device 66. Similarly, the basal rate of the basal insulin is set based on user input or in response to a command from management device 66. Infusion pump 84 may include a display for displaying pump data and a user interface providing user controls. In an alternative embodiment, insulin pump 84 and glucose sensor 56 may be provided as a single device worn by the patient, and at least a portion of the logic provided by processor 72 may reside on this single device. Bolus insulin may also be injected by other means, such as manually by the user via a needle.

Communication links 64, 86 are illustratively wireless, such as a radio frequency ("RF") or other suitable wireless frequency, in which data and controls are transmitted via electromagnetic waves between sensor 56, therapy delivery device 84, and management device 66. Bluetooth® is one exemplary type of wireless RF communication system that uses a frequency of approximately 2.4 Gigahertz (GHz). Another exemplary type of wireless communication scheme uses infrared light, such as the systems supported by the Infrared Data Association® (IrDA®). Other suitable types of wireless communication may be provided. Furthermore, each communication link 64, 86 may facilitate communication between multiple devices, such as between glucose sensor 56, computing device 66, insulin pump 84, and other suitable devices or systems. Wired links may alternatively be provided between devices of system 50, such as, for example, a wired Ethernet link. Other suitable public or proprietary wired or wireless links may be used.

Figure 3:
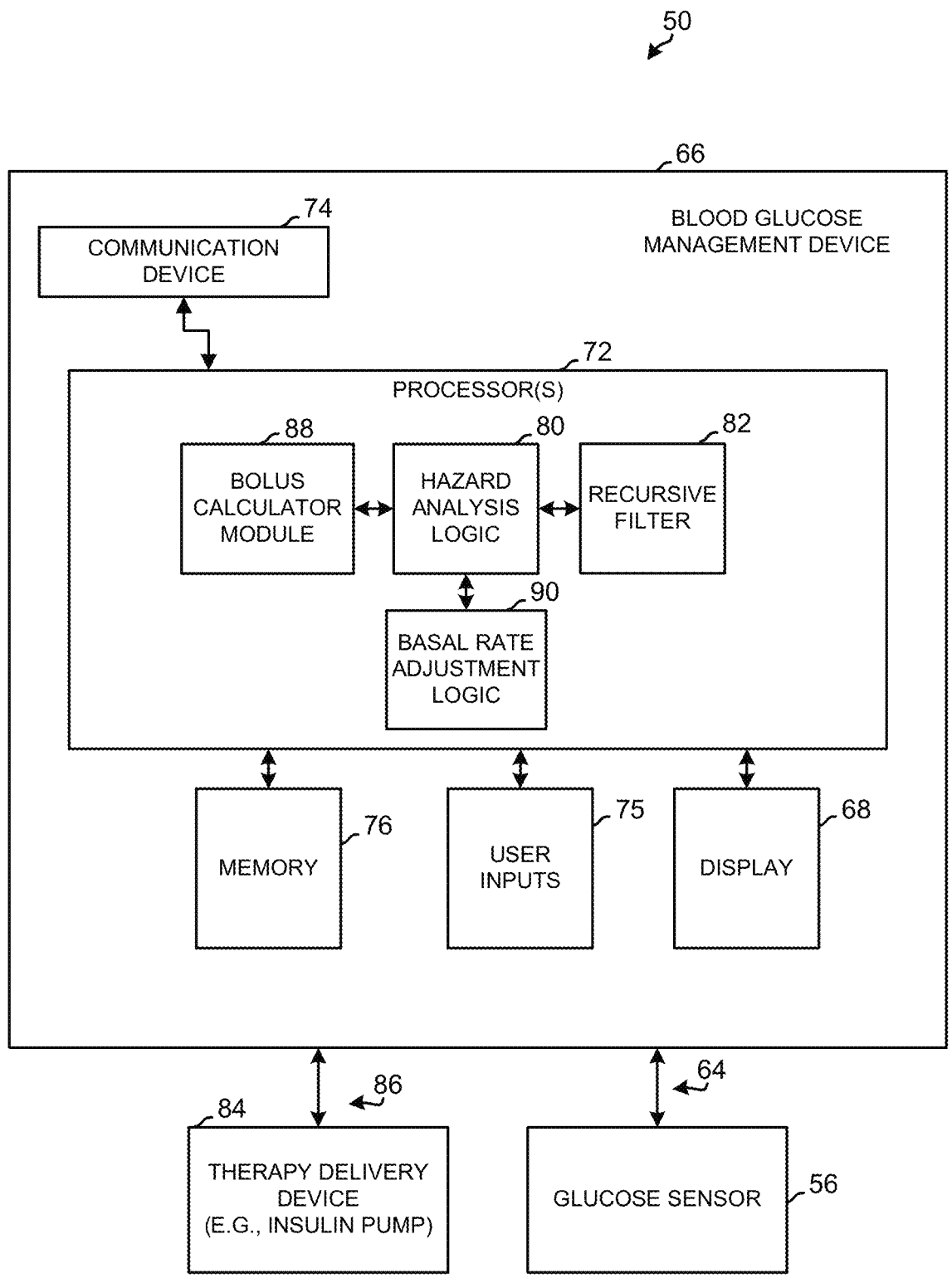
FIG. 3 illustrates an exemplary blood glucose management device, therapy delivery device, and glucose sensor of the CGM system of FIG. 2, the blood glucose management device including a bolus calculator module, hazard analysis logic, and basal rate adjustment logic.

FIG. 3 illustrates an exemplary management device 66 of the CGM system 50 of FIG. 2. Management device 66 includes at least one processing device 72 that executes software and/or firmware code stored in memory 76 of management device 66. The software/firmware code contains instructions that, when executed by the processor 72 of management device 66, causes management device 66 to perform the functions described herein. Management device 66 may alternatively include one or more application-specific integrated circuits (ASICs), field-programmable gate arrays (FPGAs), digital signal processors (DSPs), hardwired logic, or combinations thereof. While management device 66 is illustratively a glucose monitor 66, other suitable management devices 66 may be provided, such as, for example, desktop computers, laptop computers, computer servers, personal data assistants ("PDA"), smart phones, cellular devices, tablet computers, infusion pumps, an integrated device including a glucose measurement engine and a PDA or cell phone, etc. Although management device 66 is illustrated as a single management device 66, multiple computing devices may be used together to perform the functions of management device 66 described herein.

Memory 76 is any suitable computer readable medium that is accessible by processor 72. Memory 76 may be a single storage device or multiple storage devices, may be located internally or externally to management device 66, and may include both volatile and non-volatile media. Further, memory 76 may include one or both of removable and non-removable media. Exemplary memory 76 includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by management device 66.

Management device 66 further includes a communication device 74 operatively coupled to processor 72. Communication device 74 includes any suitable wireless and/or wired communication module operative to transmit and receive data and controls over communication links 64, 86 between device 66 and glucose sensor 56 and insulin pump 84. In one embodiment, communication device 74 includes an antenna 70 (FIG. 2) for receiving and/or transmitting data wirelessly over communication links 64, 86. Management device 66 stores in memory 76 measured glucose results and other data received from glucose sensor 56 and/or insulin pump 86 via communication device 74.

Management device 66 includes one or more user input devices 75 for receiving user input. Input devices 75 may include pushbuttons, switches, a mouse pointer, keyboard, touchscreen, or any other suitable input device. A display 68 is operatively coupled to processor 72. Display 68 may comprise any suitable display or monitor technology (e.g., liquid crystal display, etc.) configured to display information provided by processor 72 to a user. Processor 72 is configured to transmit to display 68 information related to the detected glucose state of the person, the risk associated with the glucose state, and basal rate and bolus information. The glucose state may include the estimated glucose level and the estimated rate-of-change of the glucose level, as well as an estimate of the quality or uncertainty of the estimated glucose level. Moreover, the displayed information may include warnings, alerts, etc. regarding whether the estimated or predicted glucose level of the person is hypoglycemic or hyperglycemic. For example, a warning may be issued if the person's glucose level falls below (or is predicted to fall below) a predetermined hypoglycemic threshold, such as 50 to 70 milligrams of glucose per deciliter of blood (mg/dl). Management device 66 may also be configured to tactilely communicate information or warnings to the person, such as for example by vibrating.

In one embodiment, management device 66 is in communication with a remote computing device, such as at a caregiver's facility or a location accessible by a caregiver, and data (e.g., glucose data or other physiological information) is transferred between them. In this embodiment, management device 66 and the remote device are configured to transfer physiological information through a data connection such as, for example, via the Internet, cellular communications, or the physical transfer of a memory device such as a diskette, USB key, compact disc, or other portable memory device.

Processor 72 includes hazard analysis logic 80 that calculates target return paths from a plurality of initial glucose states to a target glucose state based on cumulative penalty values. The target glucose state is illustratively an optimal or ideal glucose state having no associated hazard or risk, such as a glucose level of 112.5 mg/dl and a glucose rate-of-change of zero, although any suitable target glucose state may be identified. Each target return path is comprised of a plurality of intermediate glucose states that are to be encountered during a transition from the initial glucose state to the target glucose state. Cumulative penalty values, which may be calculated based on equation (1), associated with the target return paths are stored in memory 76 that may be used as a lookup table. For example, the cumulative penalty value for an initial glucose state is the sum of the static penalty value of the initial glucose state and the static penalty values of the intermediate glucose states along the target return path associated with the initial glucose state. In the illustrated embodiment, the static penalty values for each glucose state are provided by the hazard function 10 described herein with respect to FIG. 1. In one embodiment, each return path is calculated such that a total estimated hazard (e.g., cumulative penalty value) associated with the initial glucose state and the intermediate glucose states along the return path is minimized.

Based on the target return path for each initial glucose state, hazard control logic 80 calculates a plurality of risk metrics associated with each initial glucose state. The risk metrics calculated for each initial glucose state include a cumulative penalty value, an estimated total return time for a person's blood glucose to transition from the initial or current glucose state to the target glucose state along the calculated target return path, a maximum penalty value that is encountered with the glucose states along the target return path, and an estimated average penalty rate associated with the target return path. The average penalty rate for an initial glucose state is the cumulative penalty value divided by the estimated total return time. The values of the risk metrics are mapped to each glucose state and are stored as data matrices in memory 76.

Figure 4:
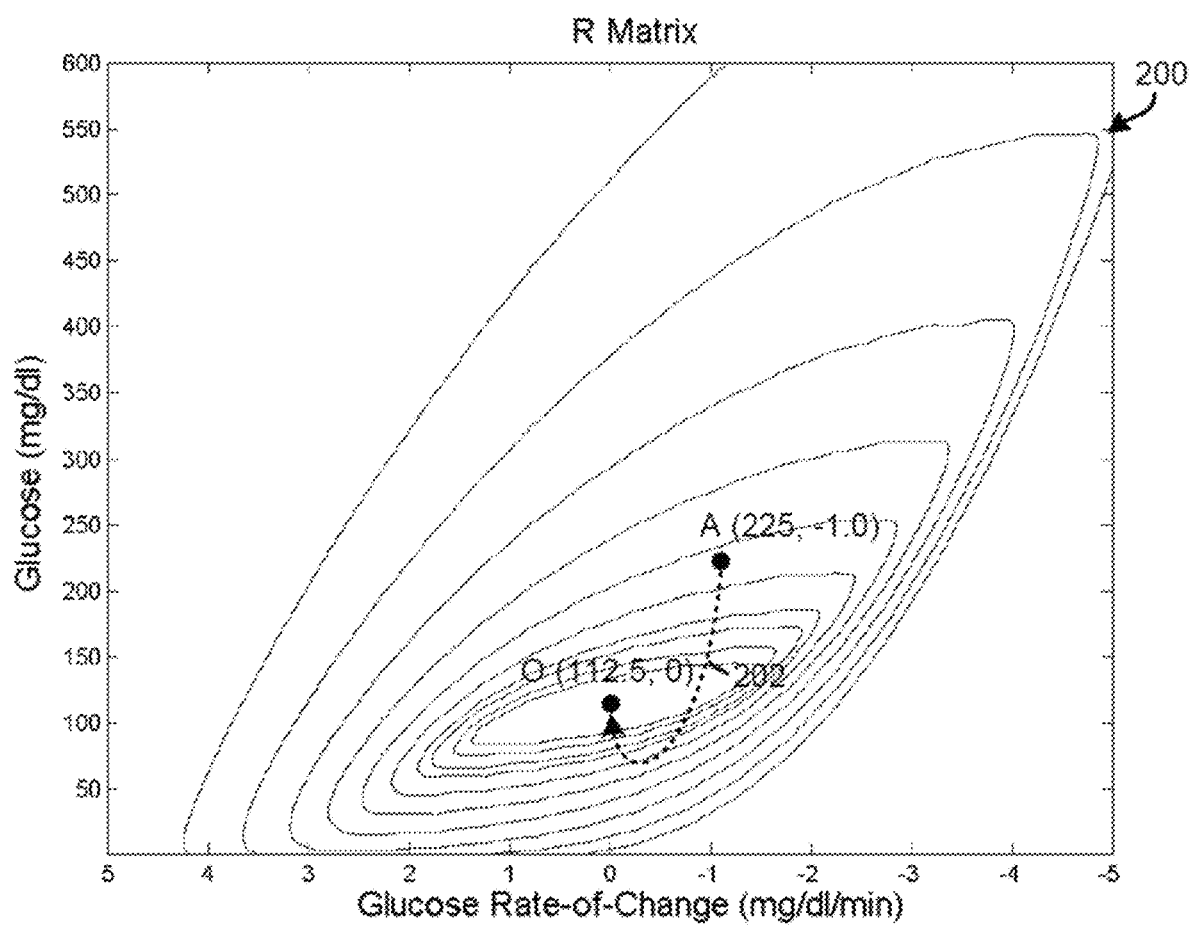
FIG. 4 illustrates a surface graph illustrating exemplary cumulative penalty values for a set of glucose states including an initial glucose state A and a target glucose state O.

The surface contour plot of FIG. 4 illustrates the cumulative penalty risk metric calculated by hazard analysis logic 80. The surface or contour illustrates the value of the cumulative penalty associated with each glucose state. Additional surface contour plots may be provided for other risk metrics, including the maximum penalty values, the estimated total return time values, and the estimated average penalty rate values. In FIG. 4, a cumulative penalty surface 200 illustrates the cumulative penalty values calculated by logic 80 for a range of glucose states. The y-axis represents the blood glucose level ranging from 0 mg/dl to 600 mg/dl and the x-axis represents the glucose rate of change ranging from −5 mg/dl/min to 5 mg/dl/min. An exemplary initial glucose state is illustrated at point A with a glucose level of 225 mg/dl and a glucose rate of change of −1.0 mg/dl/min. A target return path 202 is illustrated from the initial glucose state at point A to the target glucose state at point O. The target return path 202, calculated to minimize the cumulative penalty value of the initial glucose state, illustrates the intermediate glucose states of the calculated transition from the initial glucose state A to the target glucose state O.

Logic 80 further calculates risk surfaces or contours based on the cumulative penalty values. Each risk surface comprises risk values associated with the risk of each glucose state. Risk is calculated based on the cumulative penalty value and the probability of certainty of the glucose state.

Figure 7:
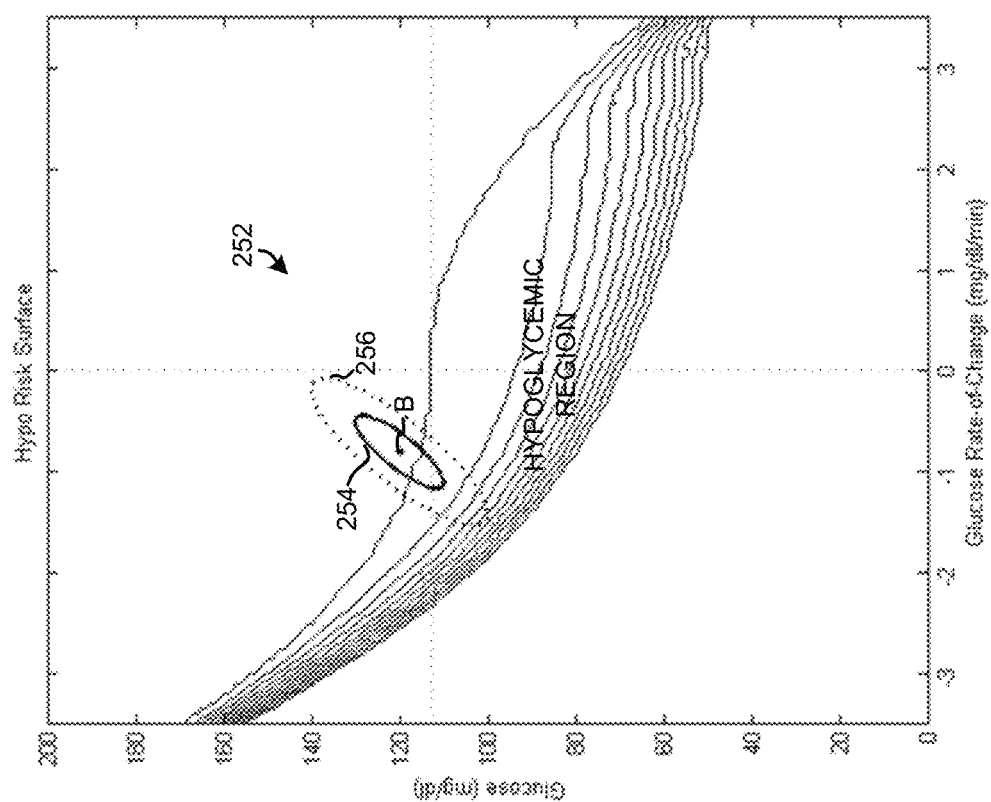
FIG. 7 illustrates a surface graph providing hypoglycemia risk values for a set of glucose states including a glucose state B.
Figure 6:
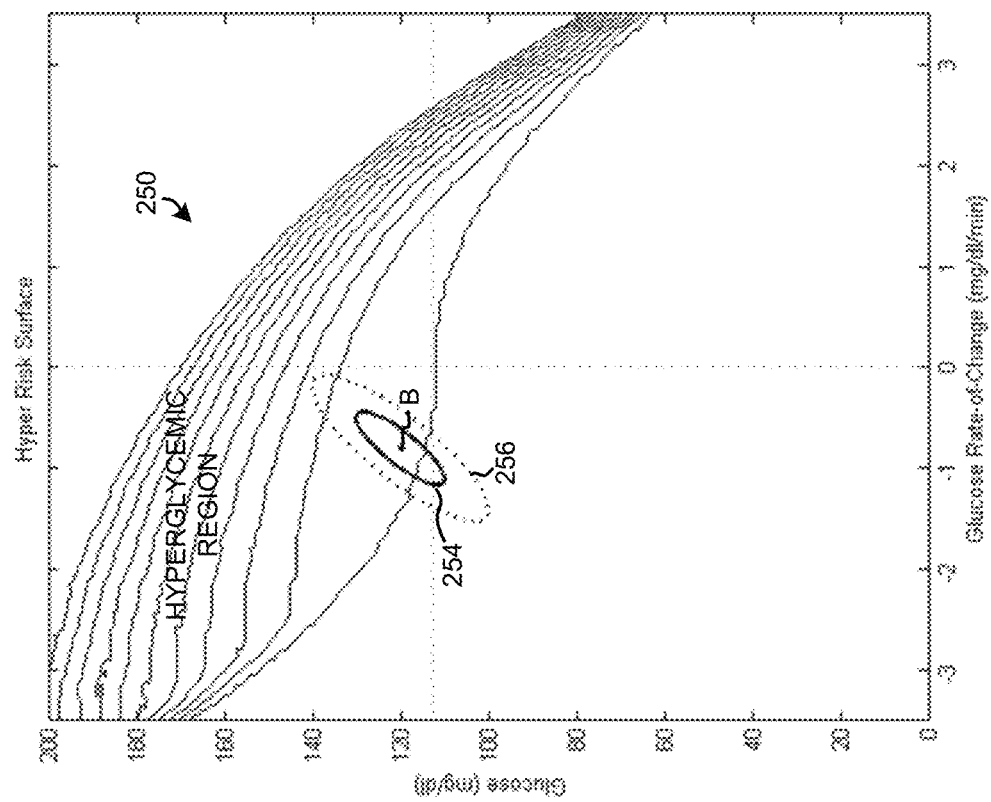
FIG. 6 illustrates a surface graph providing hyperglycemia risk values for a set of glucose states including a glucose state B.

Logic 80 of FIG. 3 is further operative to calculate signed risk/hazard metrics. In one embodiment, to calculate signed metrics, logic 80 sets the static penalty values associated with hypoglycemic glucose states, i.e., glucose states having a glucose level of less than the target glucose level, to be negative based on the following equation:

$$H_s(g) = [1.509(\log(g)^{1.0804} - 5.381)]^2 * \text{sign}[1.509(\log(g)^{1.0804} - 5.381)] \quad (2)$$

wherein g is the glucose level and $H_s(g)$ is the signed static penalty value associated with the glucose level g. The static penalty values associated with hyperglycemic glucose states remain positive. Logic 80 calculates the target return path described herein by analyzing the absolute value of the signed cumulative penalties. Based on the signed penalty values, logic 80 is operative to generate separate risk surfaces for hyperglycemia and hypoglycemia. For example, FIG. 6 illustrates a risk surface associated with hyperglycemia for a glucose state B, and FIG. 7 illustrates the risk surface associated with a hypoglycemia for the glucose state B.

In some embodiments, inaccurate glucose measurements may result from malfunction and/or noise associated with glucose sensor 56. As such, hazard analysis logic 80 analyzes the probability of accuracy of the detected glucose state provided with glucose sensor 56. Logic 80 may use any suitable probability analysis tool to determine the probability of accuracy of a measured glucose result, such as a hidden Markov model. Based on the determined probability of accuracy, hazard analysis logic 80 estimates the glucose level and the glucose rate of change of the person using a recursive filter 82 (FIG. 3). In particular, recursive filter 82, such as a Kalman filter, for example, weights the detected glucose state, including the glucose level and rate of change, with the determined probability of glucose sensor accuracy. Based on the probability of glucose sensor accuracy, recursive filter 82 calculates an uncertainty measure of the estimated glucose state. The uncertainty measure is indicative of the quality of the estimated glucose state. For a series of detected glucose states, the uncertainty for each state may vary.

A risk surface may be split into a hyperglycemia-based surface and a hypoglycemica-based surface to allow for separate risk calculations. Referring to FIGS. 6 and 7, a risk surface 250 illustrates the risk values with respect to hyperglycemia, and a risk surface 252 illustrates the risk values with respect to hypoglycemia. Upon detection of a glucose state having the glucose level and glucose rate of change corresponding to point B of FIGS. 7 and 8, logic 80 is operative to calculate the probability distribution around the detected glucose state B. FIGS. 6 and 7 illustrate two alternative distributions 254 and 256. The smaller distribution 254 indicates less uncertainty associated with the detected glucose state, while the larger distribution 256 indicates more uncertainty. Distributions 254 and 256 are illustratively Gaussian (normal) distributions, although other suitable methods of representing uncertainty may be provided, such as a particle filter or a mixture of Gaussians, for example.

Based on the uncertainty of a detected glucose state, hazard analysis logic 80 calculates a risk value for that detected glucose state. The risk value is based on the cumulative penalty value of the detected glucose state and the measure of probability of accuracy. For a given cumulative penalty of a detected glucose state, the risk value calculated by logic 80 increases with increasing uncertainty of the detected glucose state. The calculated risk value may be displayed on display 68 of management device 66. Further, the calculated risk value may be used to adjust therapy provided to the person with diabetes, such as adjusting the insulin basal rate, for example, as described herein.

For further description of calculating the target return paths and calculating risk metrics, see U.S. patent application Ser. No. 13/645,198, filed on Oct. 4, 2012, entitled "System and Method for Assessing Risk Associated with a Glucose State," the entire disclosure of which is incorporated by reference herein. For further description of the probability analysis tool, the recursive filter, the uncertainty calculation, and other probability and risk analysis functionalities of computing device 66, see U.S. patent application Ser. No. 12/693,701, filed on Jan. 26, 2010, entitled "Methods and Systems for Processing Glucose Data Measured from a Person Having Diabetes," and U.S. patent application Ser. No. 12/818,795, filed on Jun. 18, 2010, entitled "Insulin Optimization Systems and Testing Methods with Adjusted Exit Criterion Accounting for System Noise Associated with Biomarkers," the entire disclosures of which are incorporated by reference herein.

Processor 72 of FIG. 3 further includes a bolus calculator module 88 that calculates bolus recommendations and a maximum allowed glucose level of a user which may be displayed to a user via display 68. Management device 66 maintains a record in memory 76 of historical data for the user accumulated over time leading up to the current time. The historical data includes blood glucose history, prescription data, prior bolus recommendations, prior administered boluses, prior basal rates, glucose sensitivity factors for the user's sensitivity to insulin and carbohydrates, blood glucose responses to prior boluses and meal events, other user health and medical data, and the time stamp of each event and data recordation. The history data includes patient recorded information such as meal events, amount of carbohydrates consumed, confirmations of bolus deliveries, medications, exercise events, periods of stress, physiological events, manual insulin injections, and other health events, entered via user inputs 75. Bolus calculator module 88 uses the historical data to more accurately and efficiently determine the recommended insulin bolus and/or carbohydrate amount.

Bolus calculator module 88 determines a recommended bolus, such as an insulin correction bolus or a meal bolus, particular to the user based on the current glucose state, the history data, and user input. A suggested meal bolus (e.g., carbohydrate amount) may be in response to a detected or predicted hypoglycemic condition. A suggested correction bolus of insulin may be in response to the detected glucose exceeding the maximum allowable glucose level. The actual amount of carbohydrates consumed and the actual amount of insulin administered may be confirmed by the user as information entered via user inputs 75 and recorded in memory 76 with other history data. The recommended bolus may be displayed on display 68.

Figure 5:
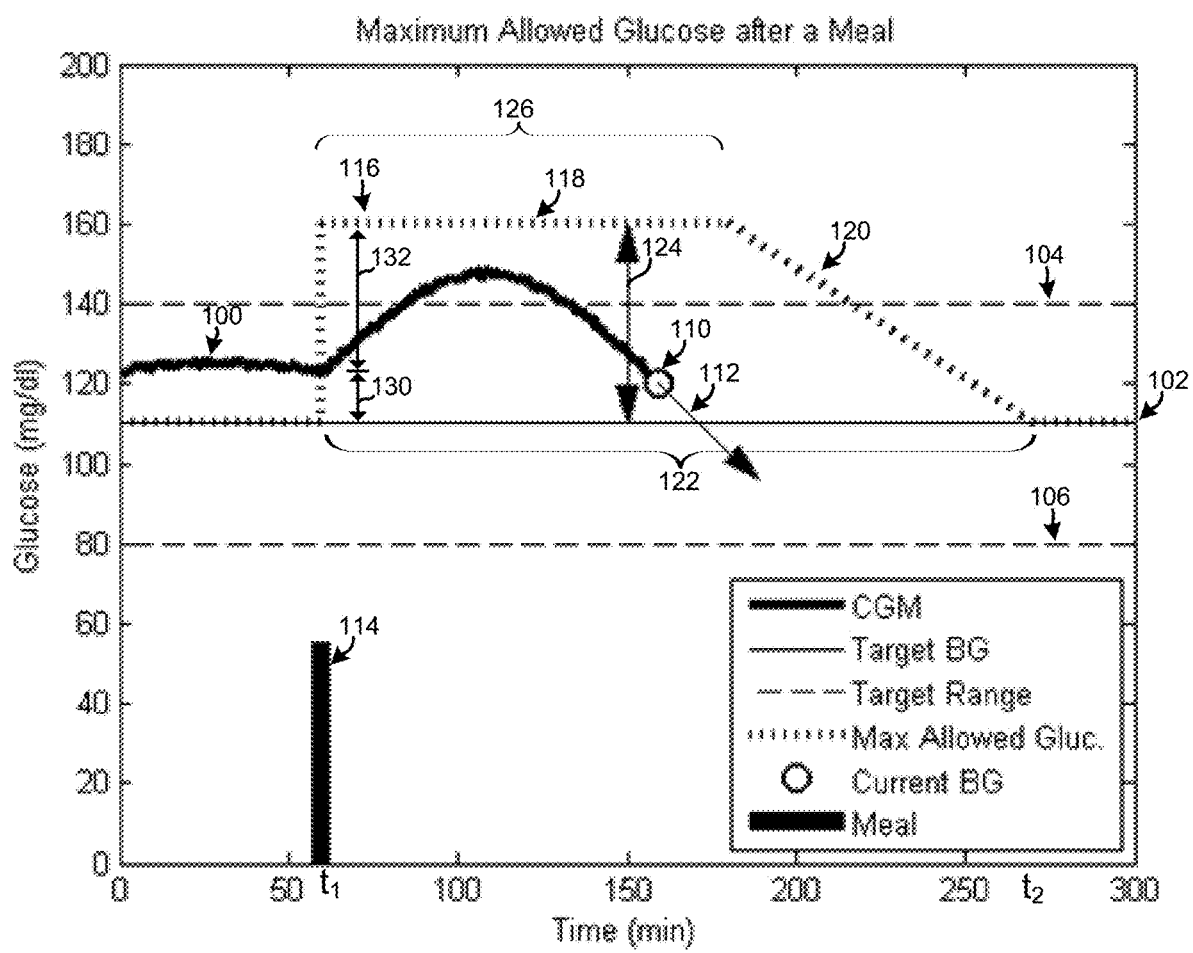
FIG. 5 illustrates a graph plotting an exemplary CGM trace and an adjusted maximum allowed glucose following a meal event.

Referring to FIG. 5, an exemplary CGM trace 100 is illustrated, wherein the x-axis represents time in minutes and the y-axis represents glucose in mg/dl. CGM trace 100 comprises a series of detected glucose levels measured over a period. In the illustrated embodiment, CGM trace 100 represents filtered glucose levels, i.e., glucose levels that are estimated based on the measured glucose levels weighted with the probably of sensor accuracy. A most recent estimated glucose level 110 has an associated negative rate of change indicated with arrow 112. Bolus calculator module 88 determines the target glucose level 102 and a target range of glucose levels indicated with an upper glucose limit 104 and a lower glucose limit 106. For illustrative purposes, target glucose level 102 is 110 mg/dl, upper glucose limit 104 is 140 mg/dl, and lower glucose limit 106 is 80 mg/dl, although other suitable values may be provided. Module 88 may determine target glucose level 102 and limits 104, 106 based at least in part on the user's history data described herein. Management device 66 uses the trending glucose data of CGM trace 100 to recommend corrective action to move the blood glucose towards the target glucose level 102. The target glucose level 102 of FIG. 5 corresponds to the maximum allowed glucose before time $t_1$ and after time $t_2$, i.e., when there has not been any recent meals or correction boluses. Between times $t_1$ and $t_2$, the maximum allowed glucose is adjusted based on a meal event 114 or other suitable events.

At time $t_1$, meal event 114 occurs when the user consumes a meal and enters carbohydrate data into management device 66 indicating the amount of carbohydrates consumed with the meal. In some instances, an insulin bolus is administered at about the time of the meal event 114 to offset the expected increase in glucose levels resulting from the meal. Bolus calculator module 88 determines a projected glucose level rise and a duration of the glucose rise based on the carbohydrates consumed, the insulin correction bolus (if administered), and the user's historical data related to glucose swings following meals and insulin injections. Based on the projected glucose rise, module 88 determines an allowed rise value 124, an offset time value 126, and an acting time value 122. The allowed rise value 124 may be based on other events, such as a glucagon injection, exercise, sleep, driving, or time of day, for example.

The allowed rise value 124 is the amount by which the glucose level of the user may be allowed to increase with respect to the target glucose level 102 as a result of the carbohydrate intake and insulin bolus. In some embodiments, the allowed rise value 124 is the combination of a correction delta glucose value 130 resulting from an insulin bolus and a meal rise value 132 resulting from the meal event 114. The correction delta glucose value 130 is the difference between the current glucose level and the target glucose level 102 at the time of the insulin bolus to allow time for the glucose level to decrease following insulin. As illustrated, the allowed rise value 124 is constant (see line 118) for a first predetermined amount of time after the meal and insulin administration, i.e., offset time 126, and then decreases linearly (see slope 120) following the offset time 126. The total time that the meal and insulin dose have an effect on the bG levels of a patient is the acting time 122. FIG. 5 illustrates a trapezoid-shaped graph 116 of the allowed rise value 124 accounting for the effect of a dose of insulin and meal event.

The maximum allowed glucose increases based on allowed rise value 124 and follows plot 116 of FIG. 5. As such, bolus calculator module 88 expands the range of allowable glucose levels after a meal event for the duration of the acting time 122 according to plot 116. The allowed rise value 124 illustratively has an initial height of 50 mg/dl, but could have other suitable heights based on the meal size, the insulin, and the user's typical reactions to boluses from the historical data. In some embodiments, for meal events above a threshold amount of carbohydrates, the meal rise value 132 is fixed. As one example, the offset time 126 is about two hours, and the acting time 122 is about three to five hours, depending on the user, the meal size, and the insulin bolus.

For further description of the bolus calculator module 88, see U.S. patent application Ser. No. 13/593,557, filed on Aug. 24, 2012, entitled "Handheld Diabetes Management Device with Bolus Calculator," and U.S. patent application Ser. No. 13/593,575, filed on Aug. 24, 2012, entitled "Insulin Pump and Methods for Operating the Insulin Pump," the entire disclosures of which are incorporated by reference herein.

As described above, hazard analysis logic 80 may generate separate risk surfaces for hyperglycemic risk and hypoglycemic risk based on the signed penalty values provided with equation (2). Using the hyperglycemic risk surface (e.g., surface 250 of FIG. 6), hazard analysis logic 80 is operative to temporarily adjust the hyperglycemic risk metric associated with the glucose states following a meal bolus and/or insulin bolus to correspond to the allowed rise value 124 and acting time 122 of FIG. 5. Logic 80 determines a theoretical glucose level by reducing the current glucose level by the amount of the allowed rise value 124 for the duration of acting time 122. The allowed rise value 124 used to shift the glucose level includes the correction meal rise value or the correction delta glucose value, or both values if both correction events occurred. Logic 80 then determines the risk metric associated with the theoretical glucose level and applies that risk metric to the current glucose level.

Figure 8:
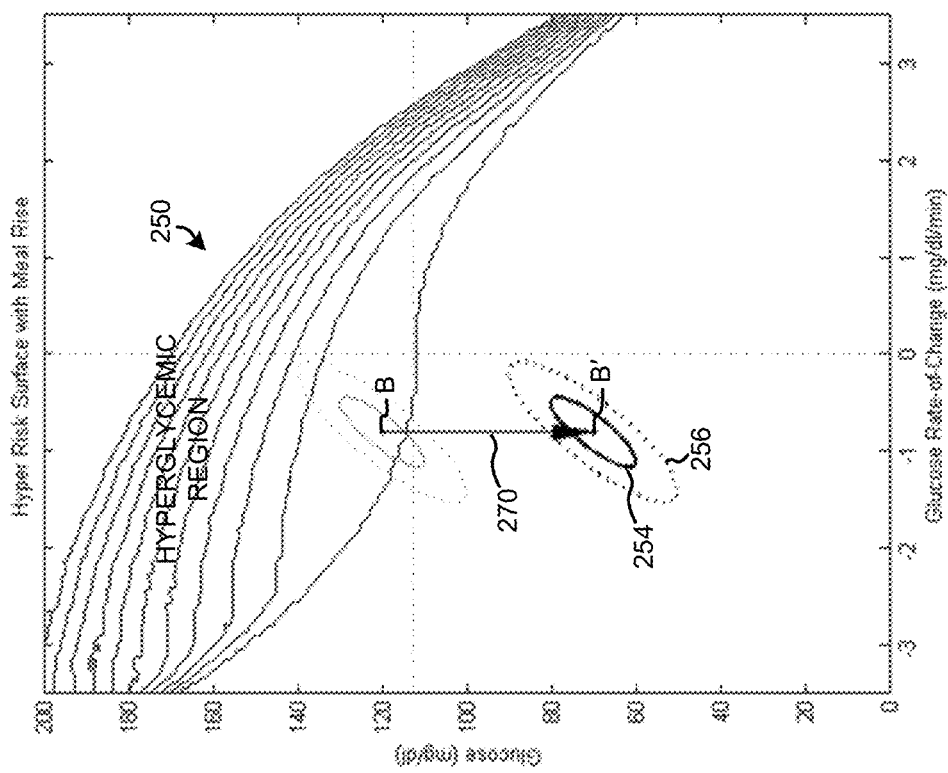
FIG. 8 illustrates the hyperglycemia-based surface graph of FIG. 6 with the glucose state B shifted down to glucose state B' based on the adjusted maximum allowed glucose of FIG. 5.

For example, FIG. 8 illustrates the estimated glucose state B of FIG. 6 shifted down to a theoretical glucose state B' by a glucose amount 270, which corresponds to the allowed rise value 124 of FIG. 5. Thus, the temporary elevation in the maximum allowed glucose provided in FIG. 5 reduces the hyperglycemic risk metrics associated with the glucose states following a meal, and logic 80 does not consider the temporary elevation in glucose after a meal as additional hyperglycemic risk if the rise is within allowable limits for a limited duration.

Figure 9:
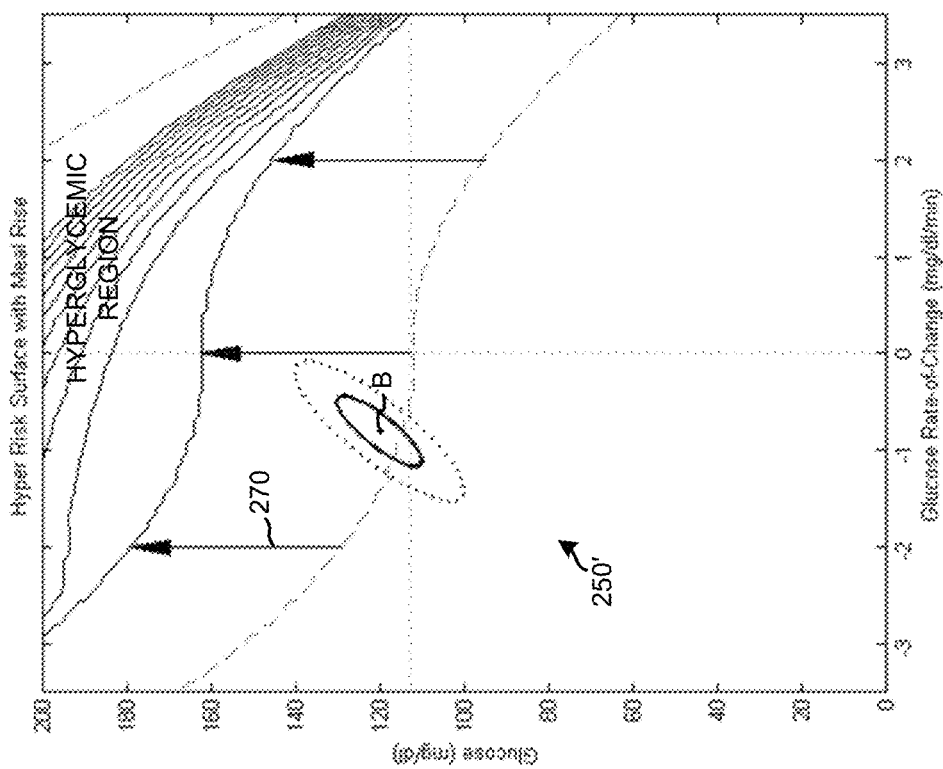
FIG. 9 illustrates the hyperglycemia-based surface graph of FIG. 6 shifted up based on the adjusted maximum allowed glucose of FIG. 5.

Alternatively, logic 80 may shift the hyperglycemic risk surface 250 upwards by shift amount 270 corresponding to the allowed rise value 124, as illustrated with hyperglycemic risk surface 250' of FIG. 9. As a result, the risk metrics associated with glucose states after the meal do not greatly increase despite the increased glucose levels resulting from the meal. While FIGS. 8 and 9 illustrate hyperglycemic risk based on cumulative penalty values (and uncertainty), other risk metrics may be adjusted similarly such as the maximum penalty value, the estimate time to return to the target glucose state, and the mean penalty rate described herein.

Logic 80 may further adjust the calculated risk associated with a estimated glucose state based on other events that potentially affect risk, such as a glucagon injection, exercise, sleep, driving, or time of day, for example.

In some embodiments, the hypoglycemic risk metrics associated with a glucose state may also be shifted as a result of the meal event and insulin bolus. For example, the hypoglycemic risk surface 252 illustrated in FIG. 7 may be shifted up if the correction insulin bolus amount exceeds the recommended dose. In this scenario, the excess insulin increases the risk of hypoglycemia. Excess insulin may also result from a manual bolus. The difference between the actual correction bolus and recommended correction bolus is converted to a glucose value using an insulin sensitivity factor. This glucose value then becomes the risk adjustment applied to the glucose state for hypo risk. The offset time and acting time remain the same. The glucose state may also be shifted due to a recent glucagon injection.

Referring again to FIG. 3, management device 66 further includes basal rate adjustment logic 90 operative to calculate and adjust a basal rate based on the current glucose state and the risk associated with the current glucose state. Management device 66 transmits an adjustment to the basal rate in a control signal to insulin pump 84 via communication link 86, and insulin pump 84 adjusts the current insulin basal rate based on the adjustment. Alternatively, the adjusted basal rate may be displayed to the user, and the user manually adjusts the basal rate of insulin pump 84. In the illustrated embodiment, the adjustment is a percent reduction to the initial, unadjusted basal rate based on a risk of hypoglycemia. Basal rate adjustments may also be made based on risk of hyperglycemic conditions.

Figure 10:
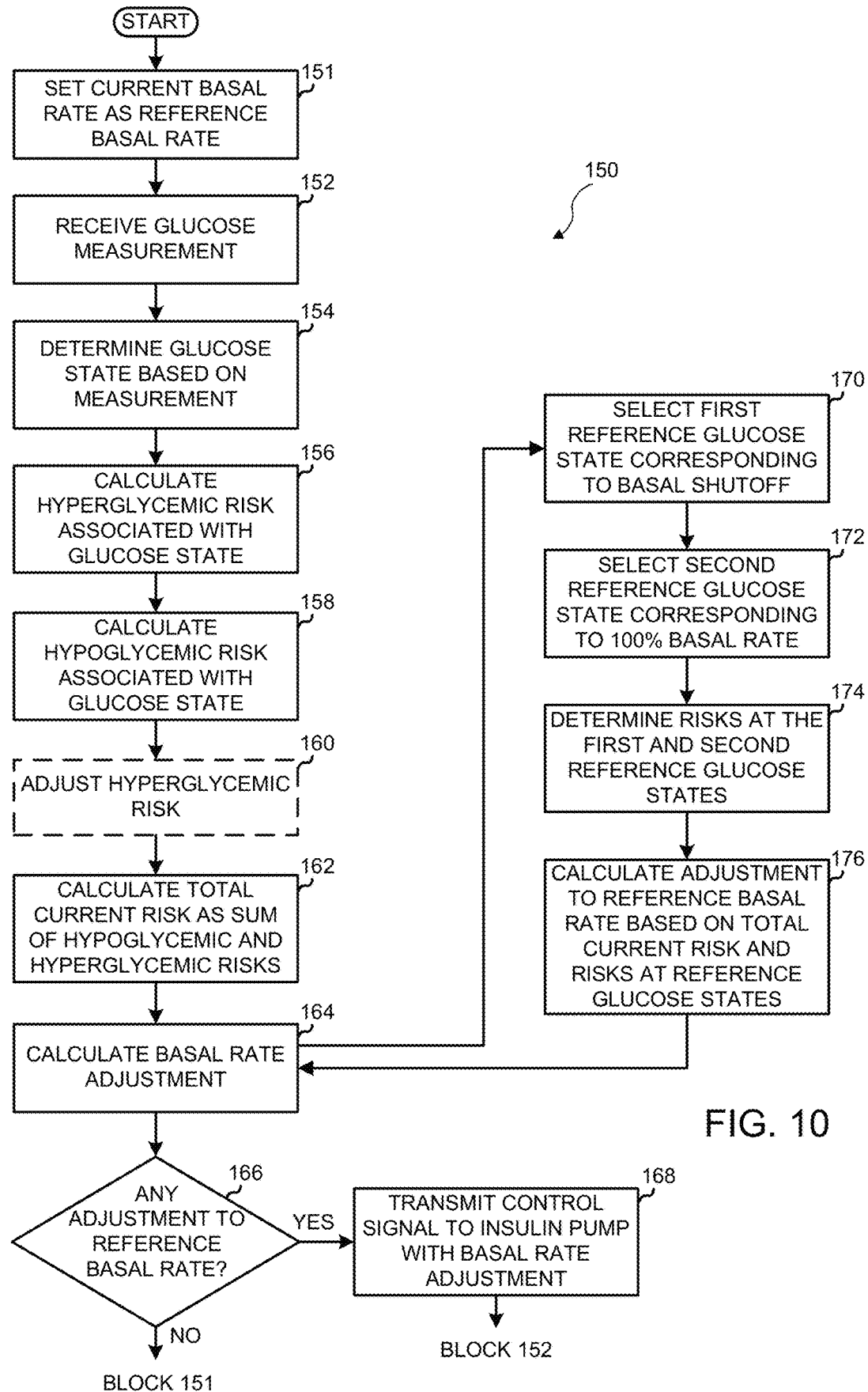
FIG. 10 illustrates a flow chart of an exemplary detailed method of operation of the blood glucose management device of FIG. 3 for adjusting the basal rate based on risk associated with an estimated glucose state.

Referring to FIG. 10, a flow diagram 100 of an exemplary method performed by management device 66 is illustrated for determining and implementing the adjustment to the basal rate based on the calculated risk of a glucose state. Reference is made to FIG. 3 throughout the description of FIG. 10. In the illustrated embodiment, the method of FIG. 10 is repeated for each glucose measurement to provide a continuously adjusted basal rate during periods of hypoglycemic risk. The operations of FIG. 10 are illustratively performed by at least hazard analysis logic 80, bolus calculator module 88, and basal rate adjustment logic 90 of processor 72.

At block 151, basal rate adjustment logic 90 identifies the current basal rate of insulin being administered to the patient by insulin pump 84 as the initial or reference basal rate. For example, the current basal rate at insulin pump 84 may be monitored by management device 66 via communication link 86 or input by a user. The current, non-adjusted basal rate is stored in memory 76 as the reference basal rate.

Referring to blocks 152 and 154, management device 66 receives a glucose measurement from glucose sensor 56 and determines the current blood glucose state of the person based on the glucose measurement, as described herein. The estimated glucose state includes the glucose level, the rate of change of the glucose level, and the measure of uncertainty or probability of accuracy. In the illustrated embodiment, hazard analysis logic 80 calculates the estimated (filtered) glucose level and rate of change based on the uncertainty measure, as described herein. At blocks 156 and 158, hazard analysis logic 80 calculates the hyperglycemic risk and the hypoglycemic risk associated with the estimated glucose state. In particular, logic 80 calculates separate hyperglycemic and hypoglycemic risk values based on the signed risk surfaces of FIGS. 6 and 7. In the illustrated embodiment, the hypoglycemia risk is a negative value and the hyperglycemia risk is a positive value. If a meal bolus and/or insulin bolus (or another event affecting risk) was recently delivered to the patient, logic 80 optionally adjusts the hyperglycemic risk of the estimated glucose state at block 160 based on the allowed rise value 124 (FIG. 5) described herein. In some embodiments, the adjusted hyperglycemic risk results in logic 90 being more responsive when an insulin bolus has been administered to the patient by adjusting the basal rate sooner and more aggressively than if an insulin bolus had not been administered. As such, the adjusted hyperglycemic risk increases the aggressiveness of the basal rate adjustment.

At block 162, hazard analysis logic 80 calculates the total current risk by summing the hyperglycemic risk and the hypoglycemic risk. If the resulting sum is a negative value, then the current glucose state has an associated hypoglycemic risk. Based on the total current risk, basal rate adjustment logic 90 calculates an adjustment to the current basal rate at block 164. Block 164 corresponds to blocks 170-176 of FIG. 10. In some embodiments, if the resulting sum is positive, then the current glucose state has an associated hyperglycemic risk and the basal rate is not reduced.

At block 170, basal rate adjustment logic 90 selects a first reference glucose state corresponding to a basal shutoff of insulin pump 84. In the illustrated embodiment, the first reference glucose state is selected to have a low glucose level at or near a minimum hypoglycemic condition, such as 50 mg/dl or 70 mg/dl or another suitable glucose level. The glucose rate of change of the first reference glucose state is illustratively zero, although another suitable glucose rate of change may be selected. Accordingly, the first reference glucose state is identified as a glucose state at which insulin pump 84 shuts off to stop the basal insulin.

At block 172, basal rate adjustment logic 90 selects a second reference glucose state corresponding to a glucose level and rate of change having no or minimal associated hypoglycemic risk and thereby no required adjustment to the current basal rate of insulin pump 84. In the illustrated embodiment, the second reference glucose state is selected to have a target glucose level of 112.5 mg/dl and zero glucose rate of change. Other suitable glucose states may be selected as the second reference glucose state. For example, the second reference glucose state may have a different glucose level with zero or nonzero associated risk.

At block 174, basal rate adjustment logic 90 determines the risk value associated with each of the first and second reference glucose states. The risk may be determined based on the risk surfaces stored in memory 76 and described herein. In the illustrated embodiment, the risks determined at block 174 each include the sum of the hypoglycemic risk and hyperglycemic risk for the corresponding reference glucose state. The risk value associated with the first reference glucose state is a negative value due to the hypoglycemic glucose level. For example, the risk value may be between −50 and −60 for a first reference glucose state having a glucose level of 50 or 70 mg/dl and zero rate of change. As described above, the risk value associated with the second reference state is zero or some minimal value. Other suitable risk values may be provided depending on the selected reference glucose states and the user's associated risk surfaces and scale.

In the illustrated embodiment, the first and second reference glucose states each have a glucose rate of change of zero. Accordingly, the risk values determined for each reference state corresponds to the risk of the corresponding glucose level at zero rate of change (constant level). Other suitable reference states may be selected that have different glucose levels and nonzero glucose rates of change.

At block 176, basal rate adjustment logic 90 calculates an adjustment to the reference basal rate identified at block 168 based on the total current risk from block 162 and the risks of the reference glucose states from block 174. In particular, basal rate adjustment logic 90 calculates a percentage or fractional reduction of the reference basal rate according to the following equation:

$$BM(R) = \begin{cases} 1, & R \geq R_{100\%} \\ \dfrac{(R - R_{0\%})}{(R_{100\%} - R_{0\%})}, & R_{100\%} > R > R_{0\%} \\ 0, & R \leq R_{0\%} \end{cases} \quad (3)$$

wherein $BM(R)$ is the adjustment factor (basal multiplier) of the reference basal rate, R is the current total risk calculated in block 160, $R_{0\%}$ is the risk value associated with the first reference glucose state, and $R_{100\%}$ is the risk associated with the second reference glucose state. When the risk value R of the current glucose state is greater than or equal to the risk value $R_{100\%}$ associated with the second reference glucose state, the adjustment factor is 1 resulting in no change to the current basal rate. In the illustrated embodiment, $R_{100\%}$ is zero resulting in no basal rate adjustment made for a glucose state having a positive risk. When the risk value R is less than or equal to the risk value $R_{0\%}$ associated with the first reference glucose state, which indicates a greater risk than the risk of the minimum glucose threshold, the adjustment factor is 0 resulting in a complete basal shutoff of pump 84 to stop insulin delivery. When the risk value R is between the risk $R_{0\%}$ associated with the first reference glucose state and the risk $R_{100\%}$ associated with the second reference glucose state, the adjustment factor is determined according to Equation (3).

At block 166, basal rate adjustment logic 90 determines whether the adjustment factor results in an adjustment to the reference basal rate, i.e., if the adjustment factor is less than 1. If no adjustment at block 166, the method returns to block 151 to again determine the current basal rate. If there is an adjustment at block 166, basal rate adjustment logic 90 calculates an adjusted basal rate at block 168 based on the reference basal rate and the adjustment factor, and management device 66 transmits a control signal to insulin pump 84 to cause pump 84 to deliver insulin at the adjusted basal rate. Alternatively, management device 66 may display the adjusted basal rate to the user to prompt the user for manual adjustment of the insulin pump 84. Following block 168, the method returns to block 152 and repeatedly executes until the adjusted basal rate returns to the unadjusted reference basal rate. In some embodiments, the implementation of the adjusted basal rate may be overridden by the user via manual control of the insulin pump 84.

Figure 11:
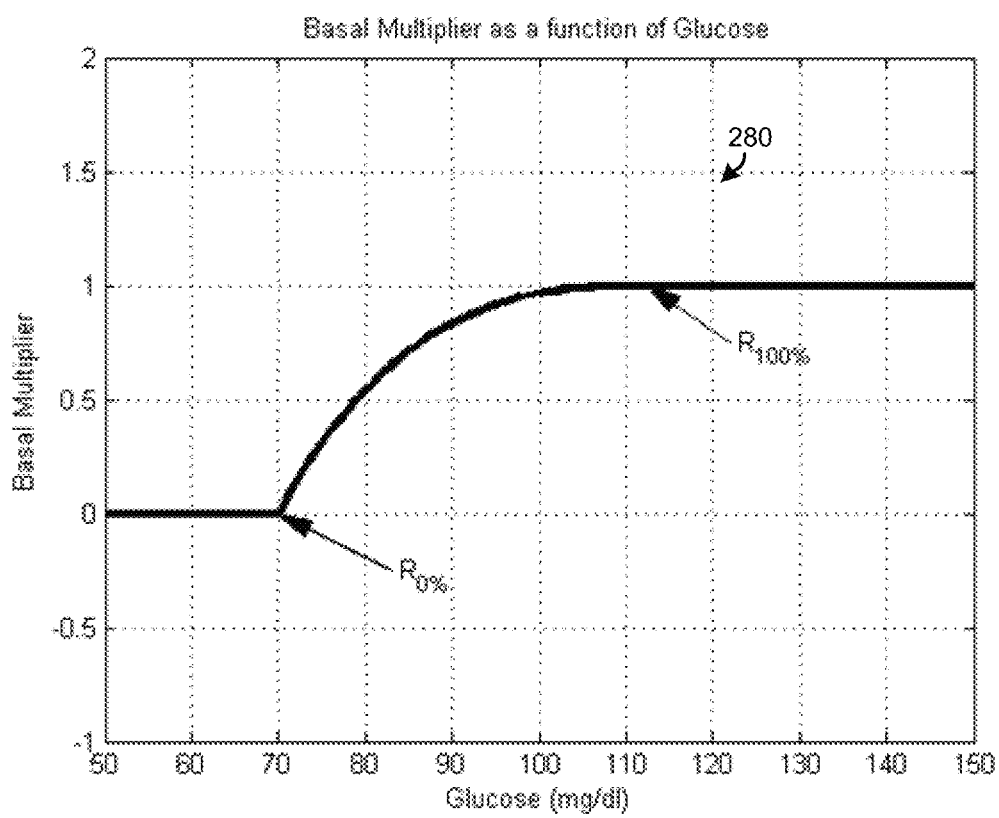
FIG. 11 illustrates a graph of a basal rate multiplier as a function of blood glucose level and a zero rate of change of the glucose level.

FIG. 11 illustrates a graph 280 of an exemplary basal rate adjustment factor (multiplier) based on the detected glucose level for the case where the rate of change of the glucose level is zero mg/dl/min. In FIG. 11, the first reference glucose state is identified as a glucose level of 70 mg/dl with zero rate of change, and the second reference glucose state is identified as a glucose level of 112.5 mg/dl with zero rate of change. Based on the risk $R_{0\%}$ associated with the first reference glucose state and the risk $R_{100\%}$ associated with the second reference glucose state, the basal rate multiplier is determined according to Equation (3). As such, for any glucose state having any glucose level and any glucose rate of change, the risk associated with that glucose state may be mapped to a basal rate adjustment according to Equation (3).

As one example, a current risk R of −30, a first reference risk $R_{0\%}$ of −50, and a second reference risk $R_{100\%}$ of zero results in an adjustment factor of ⅖ or 40% according to Equation (3). Accordingly, basal rate adjustment logic 90 multiplies the reference basal rate by an adjustment factor of 0.4 and communicates the adjusted basal rate to insulin pump 84.

Figure 12:
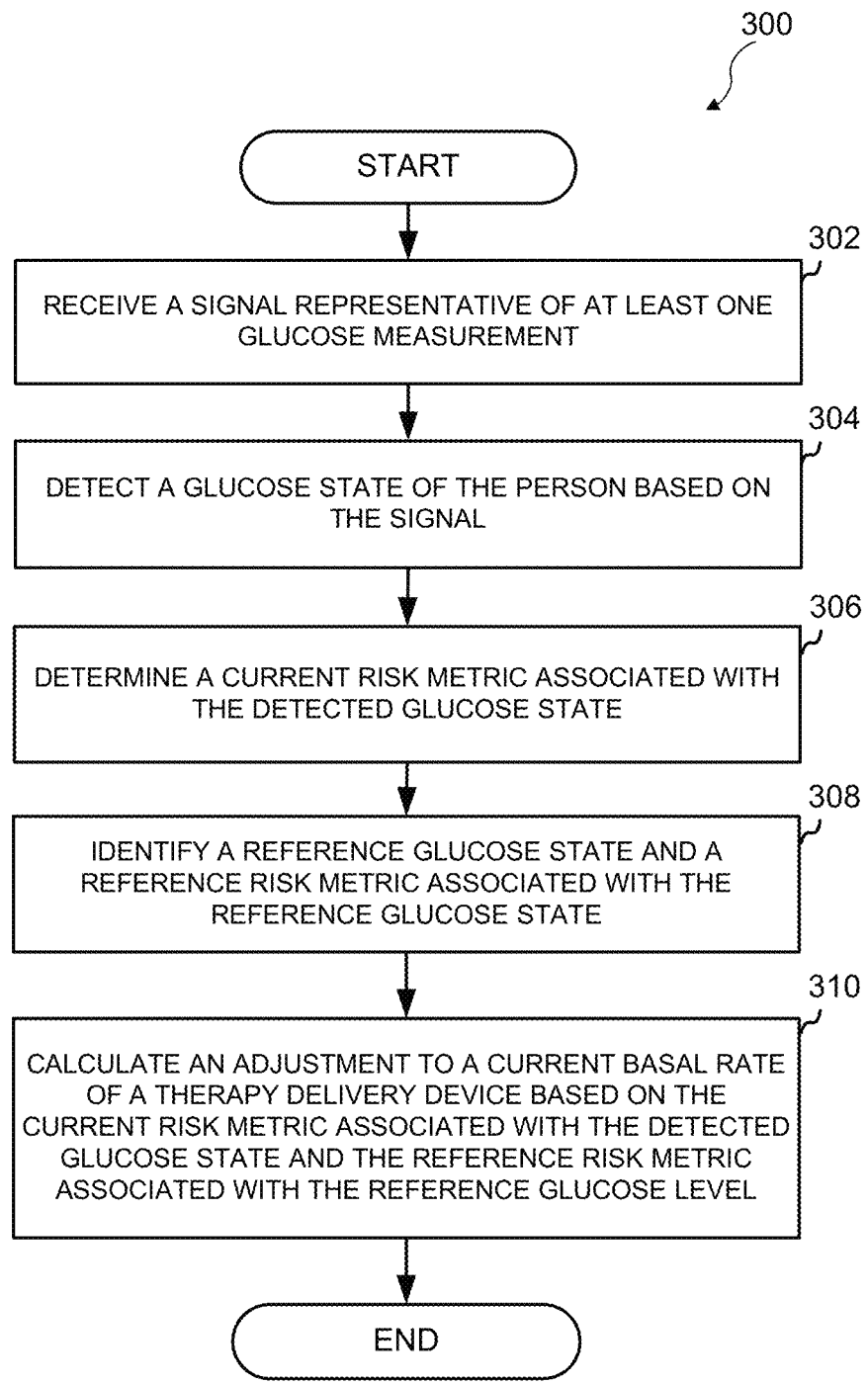
FIG. 12 illustrates a flow chart of another exemplary method of operation of the blood glucose management device of FIG. 3 for adjusting the basal rate based on risk associated with an estimated glucose state.

Referring to FIG. 12, a flow diagram 300 of another exemplary method performed by management device 66 of FIG. 3 is illustrated for calculating an adjustment to a basal rate based on risk associated with a glucose state of a person with diabetes. Reference is made to FIGS. 3 and 10 throughout the description of FIG. 12. At block 302, management device 66 receives a signal representative of at least one glucose measurement. At block 304, management device 66 detects a glucose state of the person based on the signal. The detected glucose state includes a glucose level of the person and a rate of change of the glucose level, as described herein. At block 306, management device 66 determines a current risk metric associated with the detected glucose state. The current risk metric indicates a risk of at least one of a hypoglycemic condition and a hyperglycemic condition of the person. In some embodiments, the risk metric is the risk value calculated based on the glucose level, the rate of change, and the associated uncertainty, as described herein.

At block 306, management device 66 identifies a reference glucose state and a reference risk metric (e.g., risk $R_{0\%}$) associated with the reference glucose state. At block 308, management device 66 calculates an adjustment to a basal rate of a therapy delivery device (e.g., insulin pump 84) based on the current risk metric associated with the detected glucose state and the reference risk metric associated with the reference glucose level. In the illustrated embodiment, management device 66 further identifies a second reference glucose state and a second reference risk metric (e.g., risk $R_{100\%}$) associated with the second reference glucose state, and the adjustment to the basal rate is calculated further based on the second reference risk metric. In response to the hypoglycemic risk indicated by the current risk metric R being less than a hypoglycemic risk indicated by the reference risk metric $R_{0\%}$ and greater than a hypoglycemic risk indicated by the second reference risk metric $R_{100\%}$, management device 66 generates a control signal to instruct the therapy delivery device to adjust the basal rate based on the calculated adjustment. In response to the hypoglycemic risk indicated by the current risk metric being less than a hypoglycemic risk indicated by the second reference risk metric $R_{100\%}$, management device 66 generates a control signal instructing the therapy delivery device to deliver therapy to the person at the basal rate.

In some embodiments, management device 66 displays to a user, on a graphical user interface such as display 68, graphical data representative of the calculated adjustment to the basal rate.

In some embodiments when the current risk falls between the risks of the first and second reference glucose values, the partial shutoff of insulin pump 84 serves to reduce the likelihood of the glucose state crossing the minimum allowed hypoglycemic condition (e.g., 50 to 70 mg/dl). In some embodiments when the full shutoff of insulin pump 84 occurs (when the current hypoglycemic risk is greater than the hypoglycemic risk of the first reference glucose state), basal rate adjustment logic 90 implements a pump shutoff sequence. In particular, logic 90 generates a notification to the patient after the pump 84 has been shut off for a predetermined time lapse, such as 30 minutes or another suitable time lapse. The notification alerts the patient that the pump 84 has been shut-off and that it may be advisable to take some action. A notification may also be provided immediately after the pump 84 is first shut off A notification may include a displayed warning via graphical data on display 68, an audible warning (send audible signal to a speaker device), and/or a vibration warning (send vibration command signal to a vibration device). If the basal rate remains in complete shutoff for longer than a threshold time lapse (e.g., 2 hours), then the basal rate adjustment logic 90 may be disabled, and the user receives a notification of such an event.

A predictive notification may also be given to the patient prior to pump shutoff if the risk exceeds a risk threshold and the glucose level is below a glucose threshold. An exemplary risk threshold is 1.5 times the risk metric $R_{0\%}$, and an exemplary glucose level threshold is 100 mg/dl.

If a patient responds or acknowledges a notification (e.g., via a user input 75), basal rate adjustment logic 90 displays a message on display 68 requesting that the patient eats a recommended amount of rescue carbohydrates, takes a blood glucose reading, and/or calibrates the glucose sensor if necessary. If the patient does not respond to the notification, the pump remains shut off and the blood glucose level is expected to slowly rise. If the patient does not respond to the notification after a further time lapse, and the glucose level continues to be low and/or descending further into hypoglycemia, logic 90 may generate and transmit an alarm to a glucagon kit so that the patient or care provider can be alerted to immediately inject some glucagon. The glucagon kit, which includes a computing device such as a processor and transceiver to receive and respond to the alarm, is in communication with management device 66 via any suitable communication link described herein.

In some embodiments, a temporary basal rate (TBR) is used to implement the basal rate adjustment described herein. The TBR is defined by the basal multiplier BM(R) from Equation (3) above as well as a duration for implementing the basal multiplier. Basal rate adjustment logic 90 determines the duration d for implementing the basal multiplier and a default duration $d_{max}$ of the basal multiplier if communication with therapy delivery device 84 fails or is disrupted. In this embodiment, basal rate adjustment logic 90 determines the basal multiplier based on the risk calculated for a predicted glucose level at a time in the future. The following equations apply:

$$\hat{t}_1 = d/2 \quad (4)$$

$$\hat{g}_1 = g_1 + \dot{g}_1\left(\frac{d}{2}\right) \quad (5)$$

wherein $\hat{g}_1$ is the predicted glucose value at the time $\hat{t}_1$ in the future, $g_1$ is the current estimated glucose level, and $\dot{g}_1$ is the rate of change of the current estimated glucose level. In one embodiment, the predicted rate of change associated with the predicted glucose level $\hat{g}_1$ is assumed to be constant (equal to $\dot{g}_1$). Hazard analysis logic 80 calculates the risk R for the predicted glucose level $\hat{g}_1$ and rate of change $\dot{g}_1$, and the basal multiplier BM(R) is calculated based on this predicted risk R according to Equation (3) above.

Figure 13:
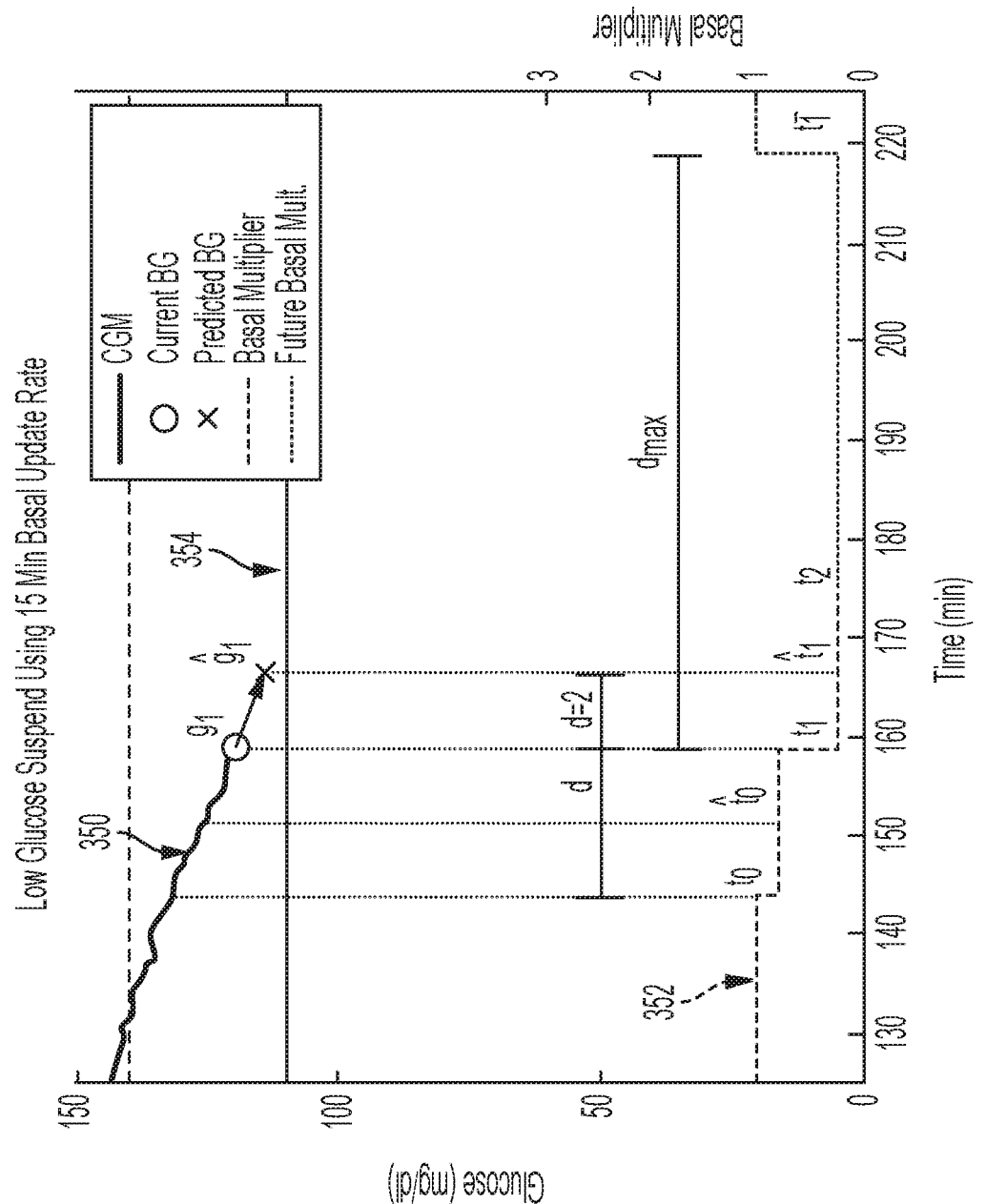
FIG. 13 illustrates a graph plotting an exemplary CGM trace and a basal rate multiplier as a function of a predicted glucose state.

After a TBR has been commanded by basal rate adjustment logic 90, the TBR is not updated in this embodiment until at least d time has passed. If the blood glucose management device 66 loses communication with therapy delivery device 84, the TBR remains in effect until $d_{max}$ time has passed. FIG. 13 illustrates an exemplary CGM trace 350 relative to a target glucose level 354, wherein the x-axis represents time in minutes and the y-axis represents glucose in mg/dl. CGM trace 350 includes a current estimated glucose level $g_1$ and a predicted glucose level $\hat{g}_1$. A basal multiplier 352 having an update rate of 15 minutes (d=15 minutes) is illustrated along the bottom of the graph of FIG. 13. Before time $t_0$, the basal multiplier 352 is equal to 1 resulting in no adjustment to the current basal rate. At time $t_0$, the basal multiplier 352 is about 0.8 for duration d until time $t_1$. At time $t_1$ a new basal multiplier 352 of about 0.2 is calculated based on the predicted glucose level $\hat{g}_1$ and the current glucose level $g_1$, as described above. The basal multiplier 352 of 0.2 is configured for implementation for duration d until time $t_2$, or for duration $d_{max}$ if communication is lost with therapy delivery device 84.

Figure 14:
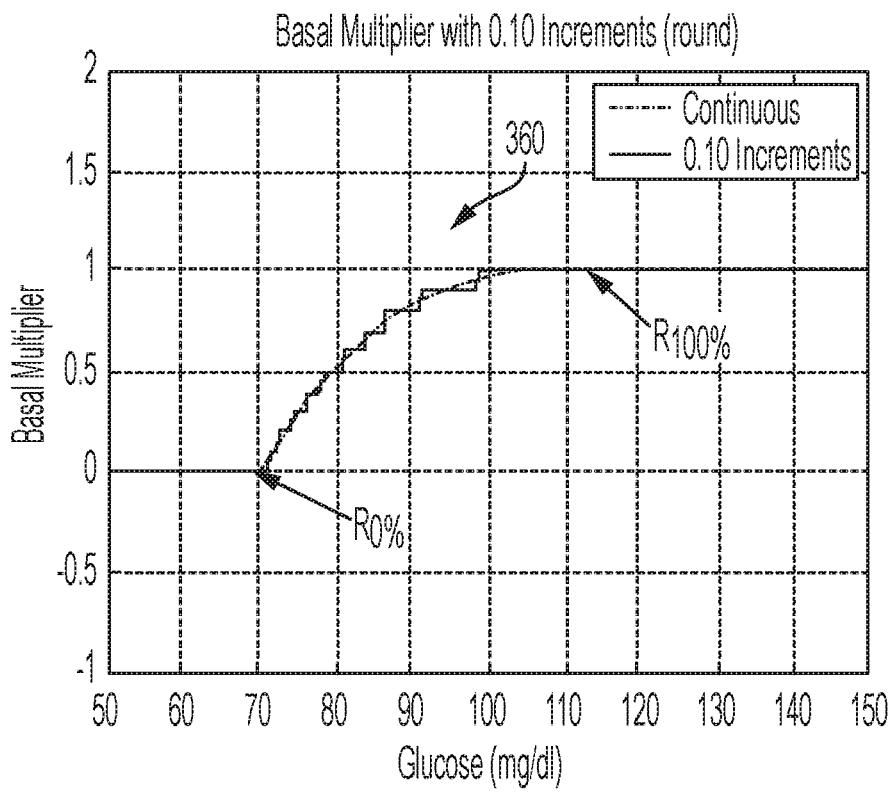
FIG. 14 illustrates a graph of an incremental basal rate multiplier using a rounding function.

In some embodiments, rather than continuous basal multiplier values, the basal multiplier may be limited to a specified incremental size, $TBR_{inc}$, such that the final basal multiplier $BM_{inc}$ is given by the following equation:

$$BM_{inc} = \text{round}\left(\frac{BM(R)}{TBR_{inc}}\right) TBR_{inc} \qquad (6)$$

wherein the increment size $TBR_{inc}$ may be 1%, 5%, 10% or any other suitable increment size, and the "round" function rounds to a specified nearest decimal place or to a whole number. As described above, FIG. 11 illustrates a graph of a continuous basal multiplier. FIG. 14 illustrates a graph of a rounded incremental basal multiplier 360 based on the rounding Equation (6). As with FIG. 11, the first reference glucose state is identified as a glucose level of 70 mg/dl with zero rate of change, and the second reference glucose state is identified as a glucose level of 112.5 mg/dl with zero rate of change. $TBR_{inc}$ is illustratively a 10% increment in FIG. 14. Based on the risk $R_{0\%}$ associated with the first reference glucose state and the risk $R_{100\%}$ associated with the second reference glucose state, the basal rate multiplier is determined according to Equations (3) and (6).

Figure 15:
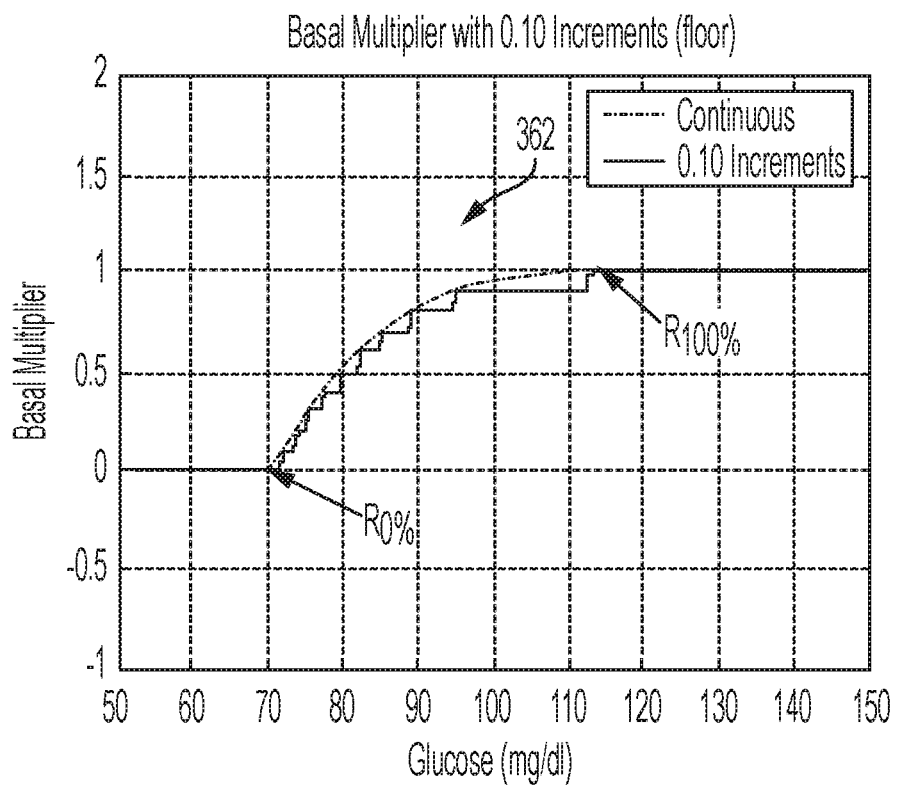
FIG. 15 illustrates a graph of an incremental basal rate multiplier using a floor function.

Alternatively, the basal multiplier may be limited to an incremental size $TBR_{inc}$ using a floor function that converts the continuous basal multiplier to an incremental basal multiplier, according to the following equation:

$$BM_{inc} = \max\left(\text{floor}\left(\frac{BM(R)}{TBR_{inc}}\right) TBR_{inc}, 0\right) \qquad (7)$$

wherein the "floor" function rounds down to the previous decimal place or whole number (e.g., floor (1.9999)=floor (1.0001)=1.0) and the "max" function outputs the greater of 0 and the floor function result, thereby avoiding a negative basal multiplier. FIG. 15 illustrates the graph of the basal multiplier of FIG. 11 modified as an incremental basal multiplier 362 based on the flooring Equation (7). $TBR_{inc}$ is illustratively a 10% increment in FIG. 15. Based on the risk $R_{0\%}$ associated with the first reference glucose state and the risk $R_{100\%}$ associated with the second reference glucose state, the basal rate multiplier is determined according to Equations (3) and (7).

As described above, FIGS. 6 and 7 illustrate respective hyper and hypo risk surfaces having state uncertainty. In some embodiments, the uncertainty of the glucose measurement may be convolved with the risk surfaces of FIGS. 6 and 7 to create a risk lookup matrix where the uncertainty is constant or close to constant. The risk calculation process may include looking up the risk value in the convolved risk lookup matrix. For example, FIG. 16 illustrates a hyper risk surface 380 that is convolved from risk surface 250 of FIG. 6 assuming constant uncertainty. Similarly, FIG. 17 illustrates a hypo risk surface 382 that is convolved from risk surface 252 of FIG. 7 assuming constant uncertainty. The risk values of risk surfaces 380 and 382 are stored in a risk lookup matrix in memory 76 of FIG. 3, where the convolved risk may be determined by looking up a particular glucose state.

In some embodiments, the full risk lookup matrix may not be used due to memory constraints. As such, a reduced risk matrix may be provided. The full risk lookup matrix is subsampled by first applying the uncertainty convolution to the full risk lookup matrix (i.e., FIGS. 16 and 17) and then selecting the appropriate subsamples. The resulting subsampled matrix has fewer stored glucose states and associated risk values. For example, an exemplary original size of the full risk matrix is 401 cells by 1199 cells, each cell storing a risk value for a corresponding glucose state, to cover glucose levels ranging from 0 mg/dl to 600 mg/dl and rates of change ranging from −5 mg/dl/min to 5 mg/dl/min. In one embodiment, the glucose level range is initially reduced to 0 to 400 mg/dl and the glucose rate of change range is reduced to −3 to 3 mg/dl/min, resulting in a reduced risk matrix size of 241 cells by 799 cells. Logic 80 adjusts the risk value of any glucose state falling outside this range to the risk value of the nearest glucose state in the range. The risk matrix may be further subsampled to any suitable reduced size by using a subsampling factor. Exemplary subsample matrices include sizes of 121 cells by 400 cells (using a subsample factor of 2), 61 cells by 200 cells (using a subsample factor of 4), 31 cells by 100 cells (using a subsample factor of 8), 15 cells by 50 cells (using a subsample factor of 16), and 7 cells by 25 cells (using a subsample factor of 32), although other suitable sizes may be provided. The memory space occupied by the subsampled risk matrix is reduced with each reduction in matrix size. Each subsampled risk matrix has a central (target) glucose rate of change of zero mg/dl/min. A subsample size may be selected to provide risk results as close as possible to the full risk matrix results while reducing memory consumption per system constraints.

After the risk matrix is subsampled to the desired size, a risk value for a detected glucose state is determined from the subsampled risk matrix using various techniques. In the illustrated embodiment, either of two methods of interpolating a risk value from the subsampled risk matrix may be implemented by hazard analysis logic 80 of FIG. 3. A nearest neighbor algorithm selects the risk value for the glucose state closest to the current detected glucose state. A bilinear interpolation method calculates an interpolated risk value using bilinear interpolation when the current detected glucose state falls within the subsampled range of glucose states. In either method, logic 80 adjusts the risk value of any glucose state falling outside the subsampled range of glucose states to the risk value of the nearest glucose state within the range.

The interpolation technique may be selected based on experimental data and simulation that provide the most accurate results as compared with the full risk matrix. In some embodiments, the bilinear interpolation produces interpolated risk values that are more accurate than the nearest neighbor values as the size of the subsampled matrix decreases due to the widening gap between subsampled glucose states.

Figure 18:
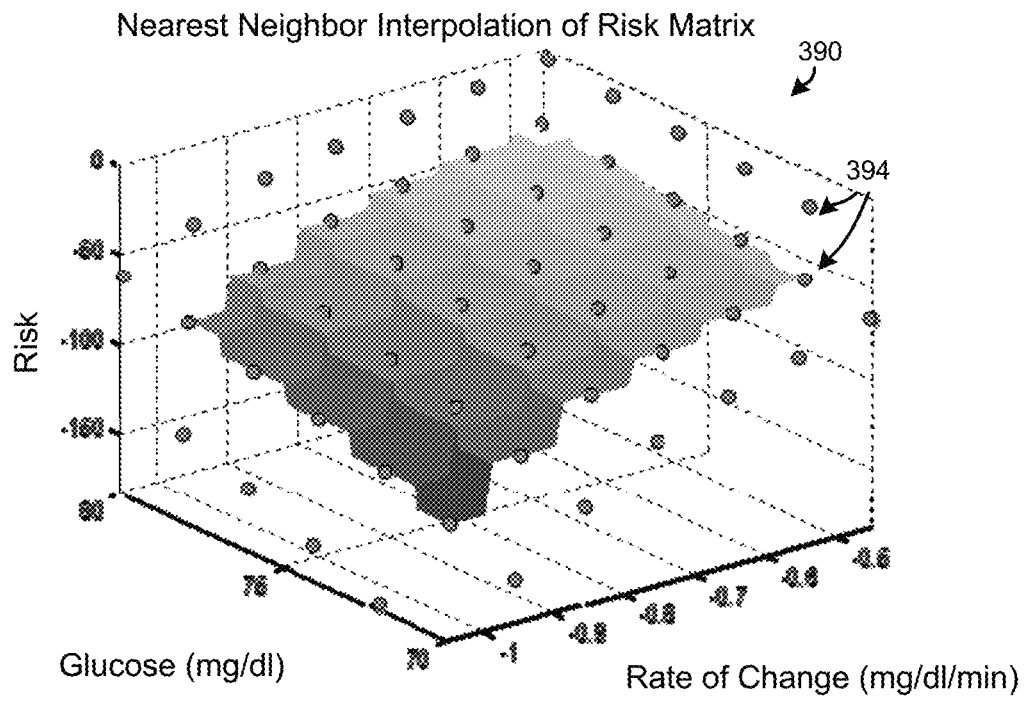
FIG. 18 illustrates a portion of a subsampled risk surface that uses a nearest neighbor interpolation method.
Figure 19:
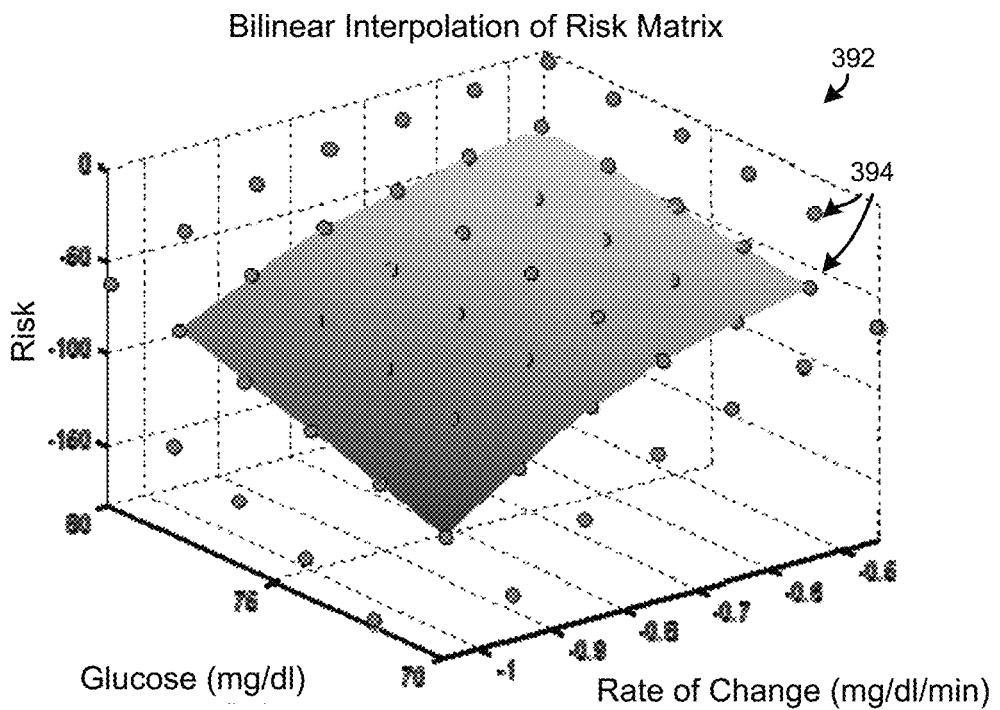
FIG. 19 illustrates a portion of a subsampled risk surface that uses a bilinear interpolation method.

FIG. 18 illustrates a portion 390 of a risk surface subsampled at the circular points 394, which represent subsampled glucose states. In FIG. 18, the risk values are interpolated from the subsampled circular points 394 using the nearest neighbor algorithm. FIG. 19 illustrates a portion 392 of the risk surface with the risk values interpolated from the subsampled circular points 394 using the bilinear interpolation algorithm. In FIGS. 18 and 19, the glucose level (mg/dl) is on the x-axis, the rate of glucose change (mg/dl/min) is on the y-axis, and the risk value is on the z-axis. In the embodiments illustrated in FIGS. 18 and 19, the bilinear interpolation method produces a smoother risk surface that more closely resembles the full risk matrix as compared with the nearest neighbor algorithm.

Figure 20:
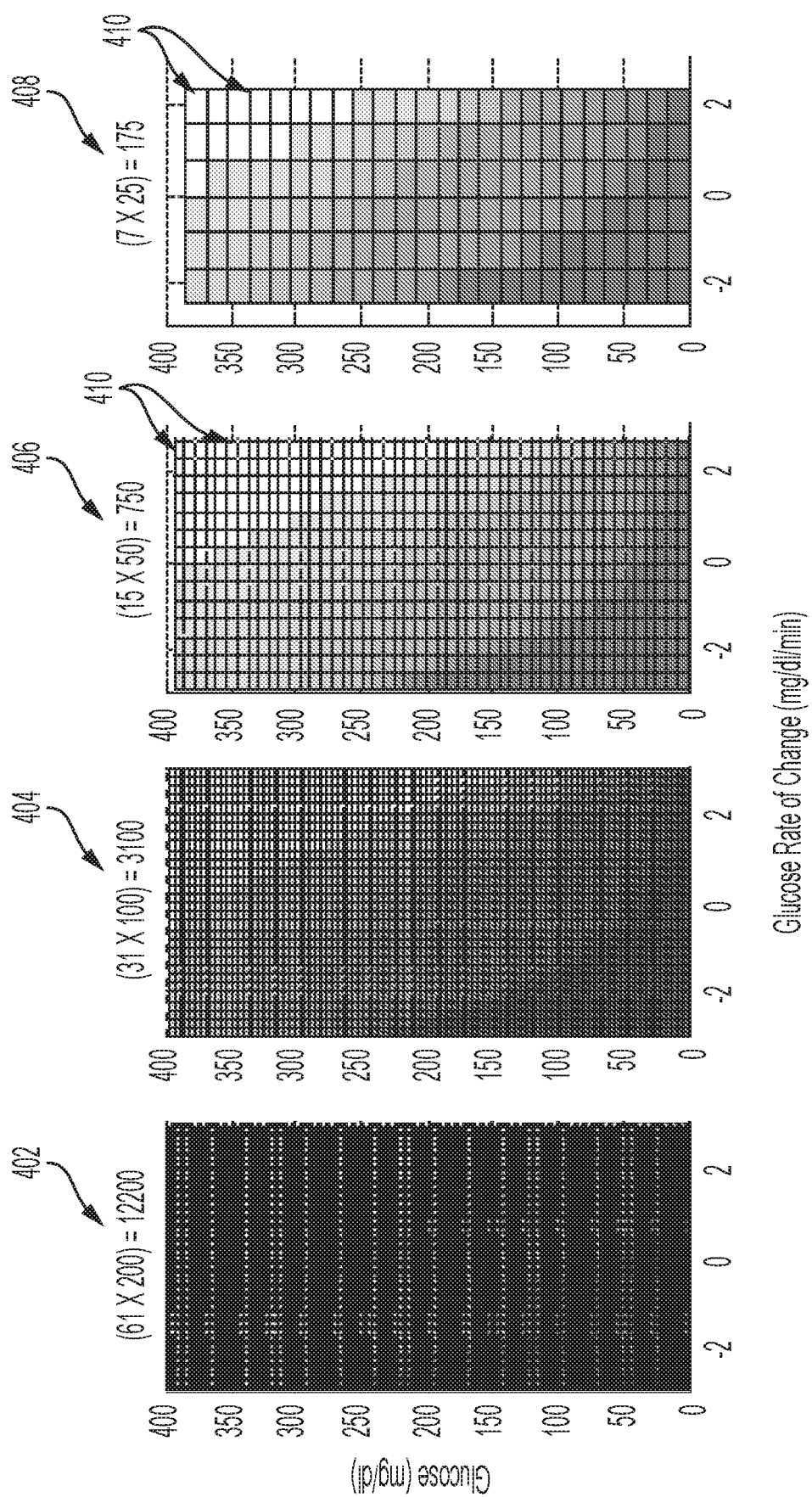
FIG. 20 illustrates several representations of subsampled risk surfaces following interpolation.

FIG. 20 illustrates several representations 402, 404, 406, and 408 of subsampled risk surfaces following interpolation. The samples are represented by the vertices of the rectangles or cells 410, as best illustrated in risk surfaces 406 and 408. Risk surface 402 has a size of 61 cells by 200 cells, risk surface 404 has a size of 31 cells by 100 cells, risk surface 406 has a size of 15 cells by 50 cells, and risk surface 408 has a size of 7 cells by 25 cells.

While the present disclosure has been described herein with respect to insulin basal rates, other suitable basal rates may be adjusted based on the methods of FIGS. 10 and 12. For example, other therapies for controlling glucose levels of diabetic people may be administered according to a basal rate which may be adjusted according to the embodiments disclosed herein.

While various embodiments of devices, systems, methods, and non-transitory computer readable medium for analyzing a glucose state and for calculating a basal rate adjustment have been described in detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

What is claimed is:

1. A method of determining a basal rate adjustment based on risk associated with a glucose state of a person with diabetes, the method comprising:
    receiving, by at least one computing device, a signal representative of at least one glucose measurement;
    detecting, by the at least one computing device, a glucose state of the person based on the signal, the detected glucose state including a glucose level of the person and a rate of change of the glucose level;
    determining, by the at least one computing device, a current risk associated with the detected glucose state based on a target glucose state, the target glucose state being stored in memory accessible by the at least one computing device, the current risk indicating a risk of at least one of a hypoglycemic condition and a hyperglycemic condition of the person;
    identifying, by the at least one computing device, a first reference glucose state and a first reference risk associated with the first reference glucose state;
    identifying, by the at least one computing device, a second reference glucose state and a second reference risk associated with the second reference glucose state;
    in response to the current risk being greater than the first reference risk and less than the second reference risk, calculating, by the at least one computing device, an adjustment to a basal rate of a therapy delivery device as a difference between the current risk and the first reference risk divided by a difference between the second reference risk and the first reference risk; and
    transmitting a control signal to instruct the therapy delivery device to adjust the basal rate based on the calculated adjustment.

2. The method of claim 1, wherein calculating an adjustment comprises mapping the current risk to a percent reduction of the basal rate.

3. The method of claim 2, wherein the first reference glucose state includes a glucose level corresponding to a hypoglycemic condition.

4. The method of claim 1, wherein the current risk is determined based on at least one penalty value associated with the detected glucose state and a probability of accuracy of the detected glucose state, and the at least one penalty value is indicative of a hazard associated with the detected glucose state.

5. The method of claim 1, wherein the current risk metric is determined based on a target transition from the current glucose state to the target glucose state, the target transition comprising at least one intermediate glucose state associated with a return to the target glucose state.

6. The method of claim 5, wherein the current risk metric is determined based on a cumulative penalty value weighted with a probability of accuracy of the detected glucose state, the cumulative penalty value including a sum of penalty values associated with a plurality of intermediate glucose states of the target transition to the target glucose state, each penalty value being indicative of a hazard associated with the corresponding intermediate glucose state.

7. The method of claim 1, further comprising, in response to the current risk less than or equal to the first reference risk, generating a control signal to instruct the therapy delivery device to stop delivering therapy to the person.

8. The method of claim 7, further comprising, following a predetermined time lapse after instructing the therapy delivery device to stop delivering therapy, generating a notification that the therapy delivery device has been stopped, the notification including at least one of graphical data displayed on a graphical user interface, an audible signal, and a vibration signal.

9. The method of claim 1, wherein a glucose level of the second reference glucose state is greater than a glucose level of the first reference glucose state.

10. The method of claim 1, further comprising displaying to a user, on a graphical user interface, graphical data representative of the calculated adjustment to the basal rate.

11. The method of claim 1, wherein the therapy delivery device includes an insulin pump for delivering insulin to the person with diabetes, and the therapy delivery device is in communication with the at least one computing device for receiving the calculated adjustment of the basal rate.

12. The method of claim 1, further comprising, prior to calculating the adjustment to the basal rate,
    identifying a target glucose level for the person;

determining at least one of a correction meal rise value and a correction delta glucose value based on a history record stored in the memory, the correction meal rise value being indicative of an amount that the glucose level of the person increases in response to a meal event, the correction delta glucose value being indicative of an amount the detected glucose level of the person decreases in response to an insulin bolus; and adjusting the current risk metric based on the at least one of the correction meal rise value and the correction delta glucose value.

13. The method of claim 12, wherein adjusting the current risk metric includes increasing a target glucose level of the target glucose state based on the at least one of the correction meal rise value and the correction delta glucose value, and determining the current risk based on the increased target glucose level.

14. A blood glucose management device configured to determine a basal rate adjustment based on risk associated with a glucose state of a person with diabetes, the device comprising:
  a non-transitory computer-readable medium storing executable instructions; and
  at least one processing device configured to execute the executable instructions such that, when executed by the at least one processing device, the executable instructions cause the at least one processing device to:
    receive a signal representative of at least one glucose measurement;
    detect a glucose state of the person based on the signal, the detected glucose state including a glucose level of the person and a rate of change of the glucose level;
    determine a current risk associated with the detected glucose state, the current risk indicating a risk of at least one of a hypoglycemic condition and a hyperglycemic condition of the person;
    identify a first reference glucose state and a first reference risk associated with the first reference glucose state;
    identify a second reference glucose state and a second reference risk associated with the second reference glucose state;
    in response to the current risk being greater than the first reference risk and less than the second reference risk, calculate an adjustment to a basal rate of a therapy delivery device as a difference between the current risk and the first reference risk divided by a difference between the second reference risk and the first reference risk; and
    transmit a control signal to instruct the therapy delivery device to adjust the basal rate based on the calculated adjustment.

15. The device of claim 14, wherein the at least one processing device calculates the adjustment by mapping the current risk to a percent reduction of the basal rate.

16. The device of claim 15, wherein the first reference glucose state includes a glucose level corresponding to a hypoglycemic condition.

17. The device of claim 14, wherein the at least one processing device determines the current risk based on at least one penalty value associated with the detected glucose state and a probability of accuracy of the detected glucose state, and the at least one penalty value is indicative of a hazard associated with the detected glucose state.

18. The device of claim 14, wherein the at least one processing device determines the current risk metric based on a target transition from the current glucose state to a target glucose state, the target transition comprises at least one intermediate glucose state associated with a return to the target glucose state, and the current risk metric is determined by the at least one processing device further based on a cumulative penalty value weighted with a probability of accuracy of the detected glucose state, wherein the cumulative penalty value includes a sum of penalty values associated with a plurality of intermediate glucose states of the target transition to the target glucose state, and each penalty value is indicative of a hazard associated with the corresponding intermediate glucose state.

19. The device of claim 14, wherein the executable instructions further cause the at least one processing device to, in response to the current risk being less than or equal to the first reference risk, generate a control signal to instruct the therapy delivery device to stop delivering therapy to the person.

20. The device of claim 19, wherein the executable instructions further cause the at least one processing device to, following a predetermined time lapse after instructing the therapy delivery device to stop delivering therapy, generate a notification that the therapy delivery device has been stopped, the notification including at least one of graphical data displayed on a graphical user interface, an audible signal, and a vibration signal.

21. The device of claim 14, wherein a glucose level of the second reference glucose state is greater than a glucose level of the first reference glucose state.

22. The device of claim 14, wherein the executable instructions further cause the at least one processing device to generate graphical data representative of the calculated adjustment to the basal rate and to display the graphical data on a display in communication with the at least one processing device.

23. The device of claim 14, wherein the executable instructions further cause the at least one processing device to, prior to calculating the adjustment to the basal rate,
  identify a target glucose level for the person;
  determine at least one of a correction meal rise value and a correction delta glucose value, the correction meal rise value being indicative of an amount that the glucose level of the person increases in response to a meal event, the correction delta glucose value being indicative of an amount the detected glucose level of the person decreases in response to an insulin bolus;
  increase the target glucose level based on the at least one of the correction meal rise value and the correction delta glucose value; and
  adjust the current risk metric based on the increased target glucose level.

* * * * *